US012757313B2

(12) United States Patent
Hill et al.

(10) Patent No.: US 12,757,313 B2
(45) Date of Patent: Oct. 6, 2026

(54) METHODS AND APPARATUS FOR GENERATING ATMOSPHERIC PRESSURE, LOW TEMPERATURE PLASMA

(71) Applicant: TellaPure, LLC, Reston, VA (US)

(72) Inventors: Edgar Bryan Hill, Ashburn, VA (US); Dawn Price, Great Falls, VA (US); Hidetaka Noda, Tokyo (JP); Masahiko Kaneko, Tokyo (JP)

(73) Assignee: TellaPure, LLC

( * ) Notice: Subject to any disclaimer, the term of this patent is extended or adjusted under 35 U.S.C. 154(b) by 0 days.

(21) Appl. No.: 17/698,299

(22) Filed: Mar. 18, 2022

(65) Prior Publication Data

US 2024/0066161 A1 Feb. 29, 2024

Related U.S. Application Data

(60) Provisional application No. 63/300,636, filed on Jan. 18, 2022, provisional application No. 63/274,848,
(Continued)

(51) Int. Cl.
*A61L 2/14* (2006.01)
*A61L 2/26* (2006.01)
(Continued)

(52) U.S. Cl.
CPC ............. *H05H 1/2418* (2021.05); *A61L 2/14* (2013.01); *A61L 2/26* (2013.01); *A61L 9/22* (2013.01);
(Continued)

(58) Field of Classification Search
CPC .. H05H 1/2418; H05H 1/2439; H05H 1/2425; H05H 1/2441; H05H 2245/36; H05H 2242/22; H05H 2245/10; H05H 1/47; H05H 1/2406; H05H 1/2431; H05H 1/46; H05H 1/48; H05H 2245/34; A61L 2/14; A61L 2/26; A61L 9/22; A61L 2202/11;
(Continued)

(56) References Cited

U.S. PATENT DOCUMENTS

2007/0205727 A1* 9/2007 Tamita .............. H01J 37/32348 315/291
2012/0229029 A1* 9/2012 Takenoshita ......... H05H 1/2406 315/111.21

(Continued)

*Primary Examiner* — Xiuyu Tai
(74) *Attorney, Agent, or Firm* — LSIP Law LLC

(57) ABSTRACT

A plasma generator generates atmospheric pressure, low temperature plasma (cold plasma), and includes a thin plate-like first electrode defining a planar bottom surface. A thin plate-like second electrode defines a planar top surface. The second electrode opposes the first electrode, such that the bottom surface of the first electrode faces the top surface of the second electrode. A first dielectric layer is disposed on the bottom surface of the first electrode, and a second dielectric layer is disposed on the top surface of the second electrode. A spacer supports the first and second electrodes to define a predetermined gap between the first and second dielectric layers. A power supply supplies electrical power to the first and second electrodes at a predetermined voltage and frequency, such that, based on the predetermined gap between the first and second dielectric layers, cold plasma is generated.

21 Claims, 9 Drawing Sheets

Related U.S. Application Data filed on Nov. 2, 2021, provisional application No. 63/231,178, filed on Aug. 9, 2021.

(51) Int. Cl.

| | |
|---|---|
| ***A61L 9/22*** | (2006.01) |
| ***H01J 37/32*** | (2006.01) |
| ***H05H 1/24*** | (2006.01) |

(52) U.S. Cl.

CPC .. *H01J 37/32009* (2013.01); *H01J 37/32825* (2013.01); *H05H 1/2425* (2021.05); *H05H 1/2439* (2021.05); *H05H 1/2441* (2021.05); *A61L 2202/11* (2013.01); *A61L 2209/14* (2013.01); *H05H 2242/22* (2021.05); *H05H 2245/10* (2021.05); *H05H 2245/36* (2021.05)

(58) Field of Classification Search

CPC .... A61L 2209/14; A61L 9/205; A61L 209/14; H01J 37/32009; H01J 37/32825; H01J 37/32559; H01J 37/32568; H01J 37/32348; H01T 19/00; B03C 3/60; B03C 3/017; B03C 3/38; B03C 3/45; B03C 3/28; B03C 3/41; B03C 3/49; B03C 3/47; B03C 2201/28; B03C 2201/30

See application file for complete search history.

(56) References Cited

U.S. PATENT DOCUMENTS

2016/0030622 A1* 2/2016 Li .............................. A61L 9/22 422/122

2021/0220662 A1* 7/2021 Liu .......................... A61N 1/44

* cited by examiner

FIG. 8

| Row | Parameter | Small Electrode (6 cm x 9 cm) | Large Electrode (30 cm x 30 cm) | Small Electrode (6 cm x 9 cm) | Large Electrode (30 cm x 30 cm) | Small Electrode (6 cm x 9 cm) | Large Electrode (30 cm x 30 cm) |
|---|---|---|---|---|---|---|---|
| 1 | Electrode Material | Aluminum | Aluminum | Aluminum | Aluminum | Aluminum | Aluminum |
| 2 | Electrode Gap | 6.0 mm | 6.0 mm | 6.0 mm | 6.0 mm | 6.0 mm | 6.0 mm |
| **3** | **Dielectric Layer Material** | **Borosilicate Glass** | **Borosilicate Glass** | **Borosilicate Glass** | **Borosilicate Glass** | **Borosilicate Glass** | **Borosilicate Glass** |
| **4** | **Dielectric Thickness (mm)** | **1.0 mm** | **1.0 mm** | **2.0 mm** | **2.0 mm** | **2.5 mm** | **2.5 mm** |
| 5 | Relative Permittivity | 4.7 | 4.7 | 4.7 | 4.7 | 4.7 | 4.7 |
| 6 | Dielectric Strength (kV/mm) | 30 kV/mm | 30 kV/mm | 30 kV/mm | 30 kV/mm | 30 kV/mm | 30 kV/mm |
| **7** | **Plasma Gap** | **4 mm** | **4 mm** | **2 mm** | **2 mm** | **1 mm** | **1 mm** |
| 8 | Frequency | 60 Hz | 60 Hz | 60 Hz | 60 Hz | 60 Hz | 60 Hz |
| 9 | Applied Voltage (AC) | 5 kV | 5 kV | 5 kV | 5 kV | 5 kV | 5 kV |
| 10 | Streamer Discharge (arbitrary qualitative scale) | 5 | 1 | 7 | 3 | 8 | 4 |
| 11 | Capacitance (farads) | 1.08E-11 F | 1.80E-10 F | 1.68E-11 F | 2.79E-10 F | 2.32E-11 F | 3.86E-10 F |
| 12 | Impedance | 2.4551E+08 ohm | 1.4730E+07 ohm | 1.5818E+08 ohm | 9.4909E+06 ohm | 1.1452E+08 ohm | 6.8712E+06 ohm |
| 13 | Peak Reduced Electric Field (Td) | 43.82 Td | 43.82 Td | 43.82 Td | 43.82 Td | 43.82 Td | 43.82 Td |
| 14 | Ignition Voltage (arbitrary qualitative scale) | 5 | 5 | 3 | 3 | 2 | 2 |
| 15 | Burning Voltage (arbitrary qualitative scale) | 4 | 4 | 2 | 2 | 1 | 1 |
| 16 | Plasma Volume/Micro-discharge number (arbitrary qualitative scale) | 1 | 16.7 | 3 | 50 | 4 | 66.7 |

FIG. 9

| Row | Parameter | Small Electrode (6 cm x 9 cm) | Large Electrode (30 cm x 30 cm) | Small Electrode (6 cm x 9 cm) | Large Electrode (30 cm x 30 cm) | Small Electrode (6 cm x 9 cm) | Large Electrode (30 cm x 30 cm) |
|---|---|---|---|---|---|---|---|
| 1 | Electrode Material | Aluminum | Aluminum | Aluminum | Aluminum | Aluminum | Aluminum |
| 2 | Electrode Gap | 6.0 mm | 6.0 mm | 6.0 mm | 6.0 mm | 6.0 mm | 6.0 mm |
| **3** | **Dielectric Layer Material** | **Ceramic** | **Ceramic** | **Ceramic** | **Ceramic** | **Ceramic** | **Ceramic** |
| **4** | **Dielectric Thickness (mm)** | **1.0 mm** | **1.0 mm** | **2.0 mm** | **2.0 mm** | **2.5 mm** | **2.5 mm** |
| 5 | Relative Permittivity | 25 | 25 | 25 | 25 | 25 | 25 |
| 6 | Dielectric Strength (kV/mm) | 24 kV/mm | 24 kV/mm | 24 kV/mm | 24 kV/mm | 24 kV/mm | 24 kV/mm |
| **7** | **Plasma Gap** | **4 mm** | **4 mm** | **2 mm** | **2 mm** | **1 mm** | **1 mm** |
| 8 | Frequency | 60 Hz | 60 Hz | 60 Hz | 60 Hz | 60 Hz | 60 Hz |
| 9 | Applied Voltage (AC) | 5 kV | 5 kV | 5 kV | 5 kV | 5 kV | 5 kV |
| 10 | Streamer Discharge (arbitrary qualitative scale) | 5 | 1 | 7 | 3 | 8 | 4 |
| 11 | Capacitance (farads) | 1.17E-11 F | 1.95E-10 F | 2.21E-11 F | 3.69E-10 F | 3.98E-11 F | 6.64E-10 F |
| 12 | Impedance | 2.2633E+08 ohm | 1.3580E+07 ohm | 1.1982E+08 ohm | 7.1895E+06 ohm | 6.6573E+07 ohm | 3.9944E+06 ohm |
| 13 | Peak Reduced Electric Field (Td) | 43.82 Td | 43.82 Td | 43.82 Td | 43.82 Td | 43.82 Td | 43.82 Td |
| 14 | Ignition Voltage (arbitrary qualitative scale) | 5 | 5 | 3 | 3 | 2 | 2 |
| 15 | Burning Voltage (arbitrary qualitative scale) | 4 | 4 | 2 | 2 | 1 | 1 |
| 16 | Plasma Volume/Micro-discharge number (arbitrary qualitative scale) | 1 | 16.7 | 3 | 50 | 4 | 66.7 |

METHODS AND APPARATUS FOR GENERATING ATMOSPHERIC PRESSURE, LOW TEMPERATURE PLASMA

BACKGROUND

Some embodiments relate to methods and apparatus for generating, dispersing, ejecting, controlling, and/or using free radicals. Some of these embodiments more specifically relate to methods and apparatus for generating the free radicals via atmospheric pressure, low temperature plasma (hereinafter "cold plasma" or "non-equilibrium plasma"). Some embodiments use these free radicals to affect or breakdown molecules into their constituent elements (such as for decomposing gases), and/or isolate or otherwise use some or all of the constituent elements, such as in the context of exhaust removal systems for example.

Cold plasma is plasma where the temperatures of the individual constituents are different from each other. Electrons exist at higher temperatures (more than 10,000K) and neutral atoms can exist at room temperature. However, the density of the electrons in cold plasma is very low compared to the density of the neutral atoms. In a laboratory, cold plasmas are generally produced by applying electrical energy to different inert gases. This production can be performed at room temperature and at atmospheric pressure, obviating costly instruments and thereby reducing the overall costs associating with making cold plasma.

On a molecular level, cold plasma is produced by moving accelerated electrons through certain gasses, e.g., helium or air. These electrons impact the atoms and molecules with so much energy that they separate the outermost electrons of the atoms and molecules in the gas, thereby creating a soupy mixture of free electrons and free ions. The gas remains at approximately room temperature because the energy required to separate the electrons from their atoms quickly dissipates, leaving the gas ions cool. The relatively low-density plasma enables controlled ionization of the available gas, which generates little to no detectable sound.

On a practical level, cold plasma is produced based on dielectric-barrier discharge (DBD), which is the electrical discharge between two electrodes separated by an insulating dielectric barrier. DBD has been referred to as silent (inaudible) discharge, ozone production discharge, or partial discharge. In the related art, DBD requires high voltage alternating current ranging from lower radio frequency to microwave frequencies. Plasma is produced by two electrodes with a dielectric layer between the electrodes to limit the current flow in the plasma. The dielectric layer that limits the current controls the rate of ionization of the gas. DBD constitutes a dry method of plasma production that does not generate wastewater or require drying of the material after treatment.

SUMMARY

Creating stable cold plasma can be difficult because it involves balancing numerous factors. For example, changes in voltage, composition of gases entering the system, air flow rate, relative humidity, electrode and insulting layer physio-chemical characteristics, introduction of catalysts, synergetic technologies, etc., can impact the production and concentration of the reactive and non-radicalized species, ions, electrons, and ultraviolet photons.

However, the potential advantages of generating stable cold plasma are enormous, because the free electrons and free ions created thereby can be selectively transmitted to impact and break down molecules. In other words, it may be beneficial to use cold plasma in a controlled manor so as to generate, disperse, eject, control, or otherwise use free radicals to selectively impact and break down certain molecules. It may also be beneficial to use free radicals to affect or break down molecules into certain constituent elements, and then isolate or otherwise use some of the constituent elements. Thus, cold plasma can be used in various applications, including ozone generation, gas reforming, and broad area low-level activation processes.

As one example, breaking down molecules of a microorganism (single cell organism) will effectively terminate the organism, thereby operating to sterilize the area in which the microorganism existed, i.e., virus inactivation. In other words, this process can effectively inactivate viruses suspended in air or on surfaces.

Breaking down molecules using cold plasma may also provide environmental benefits, such as by reducing any of the five main greenhouse gases released into the atmosphere. The massive release of these gases into the atmosphere by manufacturing and industrial processes as well as other events is a matter of serious global concern.

For example, 40% of carbon dioxide ($CO_2$) emitted into the atmosphere remains after 100 years, 20% remains after 1,000 years, and 10% remains after 10,000 years. Methane (CH4) persists in the atmosphere for far less time than carbon dioxide (about a decade), but it is more potent in terms of the "greenhouse effect" on the atmosphere. Nitrous oxide (N2O) is a powerful greenhouse gas, with a potency 300× more than that of carbon dioxide on a 100-year time scale, and it remains in the atmosphere, on average, a little more than a century. Fluorinated gases are emitted in smaller quantities than other greenhouse gases (they account for just 2% of artificially made global greenhouse gas emissions), but trap substantially more heat. Water vapor is the most abundant greenhouse gas and changes in its atmospheric concentrations are linked not to human activities directly, but rather to the warming that results from the other greenhouse gases. Carbon dioxide is the most abundant greenhouse gas released by human activities—of all carbon dioxide released in the last 250 years, approximately 40% was released on the last 40 years.

Thus, cold plasma can be used to break down the above greenhouse gases, thereby neutralizing their effect on the environment. As one example, cold plasma can be used to interact with the exhaust or byproducts of the manufacturing and industrial processes that create the greenhouse gases.

As another specific example, it may be beneficial to provide an air purification device using cold plasma, wherein a first electrode is covered with a dielectric layer, and a second electrode is similarly covered with a dielectric layer, and these electrodes/dielectrics are separated from each other by a gap in which cold plasma is generated. These electrode/dielectric layers can be formed into a matrix for scale, and an air inlet and outlet can enable air to contact the cold plasma generated in the gap to obviate viruses, pathogens, mold toxins, etc., that were disposed in the air.

The free radicals generated by cold plasma as discussed above can also be used to breakdown molecules in water and on solid surfaces. This technology may similarly be used to clean and sterilize areas and gases within internal combustion engines (ICE), waste plants, industrial mines, etc., such as by breaking down carbon dioxide into separate carbon and oxygen atoms. In these cases, only oxygen would be released, and carbon captured or sequestered. Other greenhouse gases can similarly be broken down into their constituent elements, and captured, isolated, or recombined to form less destructive or toxic compounds.

It may be especially beneficial to generate stable cold plasma with high concentrations of Reactive Oxygen Species ("ROS") and Reactive Nitrogen Species ("RNS") that are highly effective at inactivating numerous pathogens in the air, on surfaces, and in water. Additionally, reactive species, ions and electrons are relevant, important, or crucial to decomposing dangerous compounds into non-reactive compounds, chemically inert substances, and basic elements.

Cold plasma can be used on a grand scale as an active filtration system, wherein a fluid (such as air), passes through a large-area plate plasma field where the air is sterilized. An HVAC application could include a number of electrodes, such as for example eleven 20 cm×30 cm electrodes (or alternatively 30 cm×30 cm electrodes), producing 10 plasma generating fields. A singular plasma generator may process a large amount of air (such as 988-1060 cfm), and so some embodiments may use multiple plasma generators (such as combining 6 generators) to process as much fluid as is required, e.g., 5900-6360 cfm. However, as indicated above, any number of electrodes and dielectric layers can be used as well as electrodes and dielectric layers of any sizes, such as 6 cm×9 cm.

It may be beneficial to integrate the plasma generator with AQRSS (Air Quality Risk Surveillance System) technology, which allows for active testing of indoor air quality to further control the plasma generator operation. Some embodiments of the plasma generator may produce small amounts of ozone, and so the system can be configured to automatically cease operations if the output approaches CARB (0.05 ppm) or OSHA (0.1 ppm) standards (predetermined limits). Some of these embodiments may also be configured to measure gas concentrations, such as carbon dioxide, carbon monoxide, particulate matter <2.5 microns (PM 2.5), PM 1.0, Formaldehyde, Volatile Organic Compounds (VOCs), Nitrogen Oxides $(NO_x)_2$, etc.

It may be especially beneficial for the plasma generator to be configured to operate using relatively low power. For example, in some embodiments, each plasma generator operates on less than 60 watts of electrical power, which is the equivalent of a single light bulb.

Some specific embodiments relate to a plasma generator for generating atmospheric pressure, low temperature plasma. The plasma generator can include a first electrode that defines a planar bottom surface, and having a width and length that are each greater than a height extending in a height direction that is perpendicular to the planar bottom surface. A second electrode defines a planar top surface, and has a width and length that are each greater than a height extending in the height direction that is perpendicular to the planar top surface. The second electrode opposes the first electrode, such that the bottom surface of the first electrode faces the top surface of the second electrode. A first dielectric layer is disposed on at least a part of the bottom surface of the first electrode, and a second dielectric layer is disposed on at least a part of the top surface of the second electrode. A spacer supports the first and second electrodes so as to define a predetermined gap between the first and second dielectric layers. A power supply supplies electrical power to the first and second electrodes at a predetermined voltage and frequency, such that, based on the predetermined gap between the first and second dielectric layers, atmospheric pressure, low temperature plasma is generated.

In some embodiments, the power supply is configured to supply AC electrical power, and to be adjustable to provide desired AC voltages to generate stable atmospheric pressure, low temperature plasma.

In some embodiments, the power supply includes an inverter that is configured to convert DC voltage to AC voltage and is configured to output AC20V-AC100V, yielding good results between AC25V-AC45V, AC30V-AC35V, and still further at approximately AC33.3V.

In some embodiments, the inverter is configured to output a voltage with a frequency ranging from 30 Hz-90 Hz, yielding good results between 50 Hz-70 Hz, and still further at approximately 60 Hz.

In some embodiments, the power supply includes a booster that receives the output of the inverter and boosts the received voltage at a rate of 150× at 2× intervals, ranging from 3 kV-15 kV, 4 kV-7.5 kV, and still further at approximately 5 kV.

Some embodiments further include a fan configured to move a fluid (such as gas) to contact the generated plasma, and an ozone decomposition (ozonolysis) filter to separate ozone from the fluid/gas that has contacted the generated plasma.

In some embodiments, for each of the first and second dielectric layers, the relative permittivity is between 2 and 15, and thickness is between 1 mm and 3 mm.

In some embodiments, for each of the first and second dielectric layers, the relative permittivity is between 15 and 100, and thickness is less than 2 mm.

In some embodiments, for each of the first and second dielectric layers, the relative permittivity is between 100 and 500, and thickness is less than 1 mm.

In some of these embodiments that include first and second electrodes and first and second dielectric layers, the first electrode defines a top surface that is parallel to the bottom surface of the first electrode. The plasma generator can further include a supplemental first dielectric layer that is disposed on at least a part of the top surface of the first electrode, the supplemental first dielectric layer having a relative permittivity between 2 and 500, and a thickness of 3 mm or less. A third electrode defines a planar bottom surface, the third electrode having a width and length that are each greater than a height extending in the height direction that is perpendicular to the planar bottom surface. A third dielectric layer is disposed on at least a part of the bottom surface of the third electrode, the third dielectric layer having a relative permittivity between 2 and 500, and a thickness of 3 mm or less.

In some of these embodiments, the spacer is configured to support the third electrode so as to define a second predetermined gap between the supplemental first dielectric layer and the third dielectric layer, and the power supply configured to supply electrical power to all electrodes, including the third electrode, at the predetermined voltage and frequency, such that, based on the second predetermined gap between the supplemental first dielectric layer and the third dielectric layer, atmospheric pressure, low temperature plasma is generated.

BRIEF DESCRIPTION OF FIGURES

Each figure describes basic features of various methods and apparatuses for generating and/or dispersing free radicals and for separating ionized molecules. Various exemplary aspects of the systems and methods will be described in detail, with reference to the following figures, wherein:

FIG. 8 is a table of different parameters for a plasma generator embodiment with dielectric layers formed of borosilicate glass.

FIG. 9 is a table of different parameters for a plasma generator embodiment with dielectric layers formed of ceramic.

DETAILED DESCRIPTION

Figure 1:
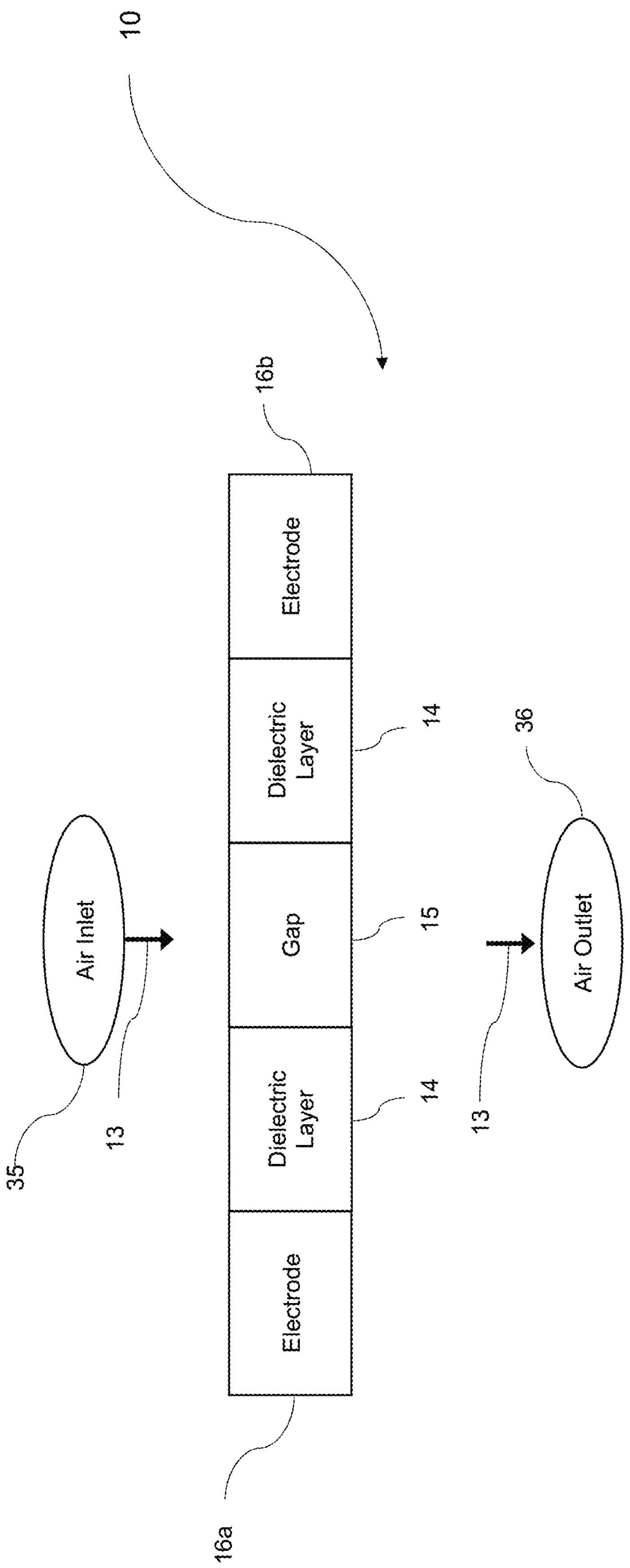
FIG. 1 is a schematic depicting basic features of a plasma generator 10 according to an exemplary embodiment.

The Detailed Description is organized based on the following headings.

- I. Definitions
- II. Plasma Generator
  - A. Applications
  - B. Overview of Plasma Generator
  - C. Variation of Embodiments
  - D. Detailed Explanation
  - E. Decreased Ozone Production
- III. Sterilization System

I. Definitions

It will be understood that, when an element is referred to as being "connected", or "coupled" to another element, it can be directly connected or coupled to the other element or intervening elements that may be present. In contrast, when an element is referred to as being "directly connected" or "directly coupled" to another element, there are no intervening elements present. As used herein "and/or" includes any and all combinations of one or more of the associated listing items. Further, it will be understood that when an element is "presented" to an entity, it can be presented electronically to the entity through multiple intermediaries or elements of the system. In addition, it will also be understood that when an element is referred to as being "directly presented" to an entity, it is presented electronically through only one intermediary or element of the system. In addition, it will be understood that when an element is presented or directly presented to an entity the presentation may take place on an electronic screen separate from any or all previous electronic screens.

It will also be understood that, although the terms "first", "second", etc. may be used herein to describe various elements or components, these elements or components should not be limited by these terms. These terms are only used to distinguish one element or component from another element or component. Thus, a first element or component discussed below could be termed a second element or component without departing from the teachings of exemplary embodiments. Further it will be understood that the use of "then", when used to describe connecting two steps of a logical process, indicates that the steps may occur sequentially, but does not preclude the addition of intermediary steps or elimination of one of the steps without departing from the teachings of exemplary embodiments.

Exemplary embodiments are described herein with reference to logical process illustrations that are schematic illustrations of idealized embodiments (and intermediate structures) of exemplary embodiments. As such, variations from the sequence of the illustrations as a result, for exemplary, of inclusion of intermediary steps, are to be expected. Thus, exemplary embodiments should not be construed as limited to the particular sequence of logical steps illustrated herein but are to include deviations in the sequence of the steps, for exemplary, from communication of electronic information to remote databases. Thus, the logical steps illustrated in the figures are schematic in nature and their sequence is not intended to limit to scope of exemplary embodiments.

The terminology used herein is for the purpose of describing particular embodiments only and is not intended to be limiting of exemplary embodiments. As used herein, the singular forms "a", "an", and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which exemplary embodiments belong. It will be further understood that all terms, such as those defined in commonly used dictionaries, should be interpreted as having a meaning that is consistent with their meaning in the context of the relevant art and will not be interpreted in an idealized or overly formal sense unless expressly so defined herein. As used herein, expressions such as "at least one of", when preceding a list of elements, modify the entire list of elements and do not modify the individual elements of the list.

Various electrical or electronic elements of the disclosed embodiments, including but not limited to the power supply and control circuitry, are intended to include or otherwise cover all processors, software or computer programs capable of performing the various disclosed determinations, calculations, etc., for the disclosed purposes. For example, exemplary embodiments are intended to cover all software or computer programs capable of enabling processors to implement the disclosed processes. In other words, exemplary embodiments are intended to cover all systems and processes that configure a document operating system to implement the disclosed processes. Exemplary embodiments are also intended to cover any and all currently known, related art or later developed non-transitory recording or storage mediums (such as a CD-ROM, DVD-ROM, hard drive, RAM, ROM, floppy disc, magnetic tape cassette, etc.) that record or store such software or computer programs. Exemplary embodiments are further intended to cover such software, computer programs, systems and/or processes provided through any other currently known, related art, or later developed medium (such as transitory mediums, carrier waves, etc.), usable for implementing the exemplary operations disclosed above.

In accordance with the exemplary embodiments, disclosed computer programs can be executed in many exemplary ways, such as an application that is resident in the memory of a device or as a hosted application that is being executed on a server and communicating with the device application or browser via a number of standard protocols, such as TCP/IP, HTTP, XML, SOAP, REST, JSON and other sufficient protocols. The disclosed computer programs can be written in exemplary programming languages that execute from memory on the device or from a hosted server, such as BASIC, COBOL, C, C++, Java, Pascal, or scripting languages such as JavaScript, Python, Ruby, PHP, Perl or other sufficient programming languages.

Some of the disclosed embodiments include or otherwise involve data transfer over a network, such as communicating various inputs over the network. The network may include, for example, one or more of the Internet, Wide Area Networks (WANs), Local Area Networks (LANs), analog or digital wired and wireless telephone networks (e.g., a PSTN, Integrated Services Digital Network (ISDN), a cellular network, and Digital Subscriber Line (xDSL)), radio, television, cable, satellite, and/or any other delivery or tunneling mechanism for carrying data. Network may include multiple networks or subnetworks, each of which may include, for example, a wired or wireless data pathway. The network may include a circuit-switched voice network, a packet-switched data network, or any other network able to carry electronic communications. For example, the network may include networks based on the Internet protocol (IP) or asynchronous transfer mode (ATM), and may support voice using, for example, VoIP, Voice-over-ATM, or other comparable protocols used for voice data communications. In one implementation, the network includes a cellular telephone network configured to enable exchange of text or SMS messages. Some of these and other embodiments utilize a Bluetooth network.

Examples of a network include, but are not limited to, a personal area network (PAN), a storage area network (SAN), a home area network (HAN), a campus area network (CAN), a local area network (LAN), a wide area network (WAN), a metropolitan area network (MAN), a virtual private network (VPN), an enterprise private network (EPN), Internet, a global area network (GAN), and so forth.

Central database systems may include a network server for communicating with the various remote computer systems. Communication to the network may be over the Internet, other networks, telephone, or other suitable means. The central database systems further include a central database and database server for storing and retrieving information. The network server can be operated by software that allows communication with the remote computer systems and transfers information to and from the database server for maintenance of the database and for providing patient specific information.

Reference will now be made in detail to embodiments, examples of which are illustrated in the accompanying schematics, wherein like reference numerals refer to the like elements throughout. In this regard, the present embodiments may have different forms and should not be construed as being limited to the descriptions set forth herein. Accordingly, the embodiments are merely described below, by referring to the figures, to explain exemplary embodiments of the present description. It is also important to note that various elements and features may be used interchangeably among the different disclosed embodiments, and so the various elements and features may be combined to achieve new embodiments.

II. Plasma Generator

Embodiments are intended to include or otherwise cover a variety of structures and processes for generating stable cold plasma for any possible advantageous use, e.g., so that the free electrons and free ions created thereby can be selectively transmitted to impact and break down molecules. Some of the disclosed plasma generator embodiments constitute large-area multi-layer dielectric barrier plasma discharge units or "reactors"; however, other embodiments can cover other types of units.

Some of the disclosed plasma generators include a first electrode covered (e.g., in part) with a dielectric layer, and a second electrode similarly covered (e.g., in part) with a dielectric layer, wherein these electrodes/dielectrics are separated from each other by a gap in which cold plasma is generated. However, embodiments are intended to cover or otherwise include other structures for generating the stable cold plasma, such as including but not limited to only one of the electrodes being covered (e.g., in part) with a dielectric layer, or alternatively multiple dielectric layers being disposed between a pair of electrodes.

In some of these embodiments, stable cold plasma is generated based on the following factors: 1) height of gap separating the electrodes/dielectrics; 2) voltage of AC electrical power supplied to the electrodes; and 3) frequency of electrical power supplied to the electrodes. However, other factors can affect the stable cold plasma generation of some embodiments, including the materials from which the electrodes and dielectric layers are formed, the relative permittivity and strength of the dielectric layer, etc. For example, in order to generate stable cold plasma, the output voltage can be controlled based on certain structural parameters of the plasma generator, such as the vertical distance separating the electrodes, the materials from which the electrodes are formed, the plane size and thickness of the electrodes, etc.

In addition, embodiments are intended to cover or otherwise include any combination of the above factors that achieves the generation of stable cold plasma, including but not limited to the exemplary ranges specifically disclosed herein. Still further, embodiments are intended to include or otherwise cover any methods, processes, or structures for supplying, varying or otherwise modifying the electrical power to the electrodes having appropriate voltages and frequencies for generating the stable cold plasma.

A few exemplary plasma generator embodiments are disclosed below, however as indicated above, embodiments are intended to cover many different variances in structure and function from the specific elements and processes disclosed below.

A. Applications

Embodiments are intended to cover various structures of plasma generators for creating or otherwise generating free electrons and free ions, such as to selectively transmit the generated free electrons and free ions to impact and break down molecules for any useful purpose. Embodiments are also intended to be configured for use with any advantageous or otherwise beneficial applications of the stable cold plasma and the free electrons and free ions generated thereby. For example, embodiments are intended to include or otherwise cover any advantageous or otherwise beneficial application of using the generated free electrons and free ions to break down or otherwise modify molecules.

For example, embodiments can be used in various contexts related to disinfection, including viral inactivation. This usage may be especially poignant based on the fact that droplet transmission is associated with the spread of coronavirus and similar pathogens including other viruses, pathogenic bacteria, mold, poisons, gases, mycotoxins (aerosol infection) constitutes one of the main routes of infection. Thus, it may be beneficial to structure or otherwise use the plasma generator embodiments disclosed herein to contact air that may include such pathogens and thereby sterilize the air to reduce, minimize, or prevent the transmission and spread of the pathogens.

Embodiments are intended to include or otherwise cover any structures or processes that enable or otherwise adapt the disclosed plasma generators for such sterilization usages. For example, the disclosed plasma generators can be adapted to operate in conjunction with equipment configured to supply air to the generated plasma, and then to export the sterilized air back into the environment in which the air was originally obtained.

For some of these embodiments that operate as air sterilizers, additional structures may be provided for enhanced sterilization, such as apparatus for increasing turbulence of air upon entering an inlet into the gap in which the cold plasma is generated. The increased turbulence increases the contact rate of the air with the electrons and ions to enhance sterilization.

A number of electrodes for generating cold plasma can be arranged into a matrix to scale the sterilization process. In other words, a plurality of plasma generating units (each of which can be planar), can be stacked and otherwise provided to ensure that collected ambient air is efficiently mixed with the plasma to enhance sterilization.

However, embodiments are intended to cover or otherwise include any other useful application of creating or otherwise generating free electrons and free ions, including but not limited to selectively transmit the generated free electrons and free ions to impact and break down molecules.

For example, some embodiments are directed to breaking down greenhouse gasses in any possible context, such as in the exhaust of industrial and manufacturing facilities (e.g., coal plants, cement manufacturing, etc.), internal combustion engine operations (e.g., automobiles), etc. Still other embodiments are directed to breaking down molecules via a liquid, including water-based liquids, such as in the contexts of waste-water treatment, using water to sterilize various things including but not limited to cloths, farm animals, etc. Other embodiments are directed to still other applications, such as sterilizing currency.

B. Overview

FIG. 1 is a schematic depicting basic features of a plasma generator 10 according to an exemplary embodiment wherein the various elements are schematically shown in the context of their relative positioning. As shown in FIG. 1, the plasma generator 10 includes a pair of electrodes 16*a*, 16*b* at opposing sides of the plasma generator 10.

In some of the disclosed embodiments, the electrodes 16*a*, 16*b* are each planar (flat) conductive metal plates. However, embodiments are intended to include or otherwise cover any type of electrical conductor that is usable to make contact with a metallic part of a circuit configured to generate stable cold plasma. For example, in some embodiments, the electrodes 16*a*, 16*b* are solid metal while in other embodiments the electrodes 16*a*, 16*b* are formed as a mesh that defines gaps therewithin. Also, it is intended that the electrodes 16*a*, 16*b* can be formed of any related art, known, or later developed material that operates as a suitable electrical conductor suitable for the purpose of generating stable cold plasma.

In some embodiments, the electrode is the circuit element that allows current to pass through its volume to its surface, but the electrons stay confined to the surface and cannot pass through the dielectric material directly opposite the incoming current. Similarly, the electrons are allowed to pass from the surface of the electrode through its volume, without any electrons passing through the dielectric material to the electrode surface opposite an outgoing current.

In some embodiments, the electrodes 16*a*, 16*b* have the same structure, size, and shape. For example, both electrodes can be formed into the same or substantially the same size and planar shape, where each defines a rectangle, square, etc., in top plan view. However, in other embodiments, the electrodes 16*a*, 16*b* can have different shapes and sizes, and can be formed of different materials.

As shown in FIG. 1, a pair of dielectric layers 14 is disposed between both electrodes 16*a*, 16*b*. However, in some embodiments, only one dielectric layer 14 is disposed between the electrodes 16*a*, 16*b*. Also in some embodiments, each dielectric layer 14 is laminated onto one, or both, of the electrodes 16*a*, 16*b*. In some embodiments, each dielectric layer 14 is disposed directly on one of the electrodes 16*a*, 16*b*, such as in cases where the dielectric layer 14 is laminated or otherwise integrally formed onto the electrode 16*a*, 16*b*. However, in some other embodiments, each dielectric layer 14 can be separated from the nearest electrode 16*a*, 16*b*, such as where an empty gap extends therebetween or alternatively where another element extends therebetween. In other words, embodiments are not limited to structures where the dielectric layers are necessarily in direct contact with electrodes, and some embodiments may even cover structures where other elements are disposed between electrodes and dielectric layers.

Embodiments are intended to include or otherwise cover the dielectric layer(s) 14 as constituting any electrical insulator that can be polarized by an applied electric field, such that when the dielectric material is placed in an electric field, electric charges do not flow through the material as they do in an electrical conductor (in this case the electrodes 16*a*, 16*b*), so as to thereby be usable with the other elements of the plasma generator 10 to generate stable cold plasma.

More specifically, the dielectric layer(s) 14 are envisioned to be formed of any related art, known, or later developed material without (or with reduced) loosely bound (or free) electrons that may drift through the material, and that instead shift (slightly), from their average equilibrium positions, causing dielectric polarization. Because of this dielectric polarization, positive charges are displaced in the direction of the field and negative charges shift in the direction opposite to the field (for example, if the field is moving parallel to the positive x axis, the negative charges will shift in the negative x direction, so as to create an internal electric field that reduces the overall field within the dielectric itself. In embodiments where the dielectric is composed of weakly bonded molecules, those molecules not only become polarized, but also reorient so that their symmetry axes align to the field.

In some embodiments, the dielectric layers 14 have the same structure, size, and shape. For example, both dielectric layers 14 can be formed into the same or substantially the same size and planar shape, where each defines a rectangle or square in top plan view. However, in other embodiments, the dielectric layers 14 can have different shapes and sizes and can be formed of different materials.

In some embodiments, there can be one or two dielectric layers between each pair of electrodes, yielding good results when there are two dielectric layers between each pair of electrodes. The number of electrodes can also vary, wherein the horizontally aligned electrodes are stacked vertically with dielectric layers and fluid gaps between every stacked electrode such that first and second electrodes serve as top and bottom electrodes to adjoin one plasma gap in a stack of electrodes and dielectric layers to create multiple plasma gaps. The number of electrodes can be configured to be between two and fifty-one, where the number of gaps between electrodes can be between one and fifty, yielding good results with the number of fluid gaps between five and twenty, and still further at ten.

As shown in FIG. 1, a gap 15 is defined between the dielectric layers 14. In some embodiments, the range of the gap 15 between the dielectric layers is approximately 1.5 mm to approximately 3.0 mm. In some of these embodiments, the gap 15 between the dielectric layers is approximately 1.75 mm to approximately 2.25 mm. In some of these embodiments, the gap 15 between the dielectric layers is approximately 2.0.

Electrical power at a predetermined AC voltage and frequency can be applied to the first and second electrodes 16*a*, 16*b*, such that, based also on the height of the gap 15 and other factors, stable cold plasma is generated within the gap 15. Other factors that affect the generation of cold plasma within the gap 15 include (but are not necessarily limited to) material from which the electrodes 16*a*, 16*b* are formed, plane size and thickness of the electrodes 16*a*, 16*b*, aspects of the dielectric layer 14, etc. Thus, in some embodiments, in order to generate stable cold plasma, the output voltage needs to be controlled based on certain structural parameters of the plasma generator 10, such as distance between electrodes 16*a*, 16*b* (i.e., gap 15), the material from which the electrodes 16*a*, 16*b* are formed, the plane size and thickness of the electrodes 16*a*, 16*b*, aspects of the dielectric layer 14, etc. In other words, stable cold plasma can be generated within the gap 15 based on the following factors: 1) height of gap 15 separating the electrodes/dielectrics; 2) voltage of AC electrical power supplied to the electrodes 16*a*, 16*b*; 3) frequency of electrical power supplied to the electrodes 16*a*, 16*b*; and/or 4) structural characteristics of the plasma generator 10 including but not limited to the above structural factors.

FIG. 1 also shows an airflow path 13 that enables air to flow from an air inlet 35, into the gap 15 and thus in contact with the free electrons and free ions generated by the cold plasma, and then out of an air outlet 36. Molecules that come into contact with the free electrons and free ions of the cold plasma are thereby broken down or otherwise altered.

Multiple plasma generators 10 that have the same or similar structures to those discussed above can be provided to scale the amount of cold plasma generated. In some of these embodiments, the layers of electrodes 16*a*, 16*b* and dielectrics 14 can be stacked so as to result in a vertically aligned structure, wherein a separate gap 15 separates each layer of an electrode 16*a*, 16*b* laminated with a dielectric layer 14.

Some of the embodiments create stable cold plasma by focusing on various parameters, calculations, and the application. For example, some embodiments are directed to a multi-layered dielectric barrier plasma discharge generator with a gap for approximately 2 mm. Some of these embodiments are equipped to sterilize and decompose large volumes of atmospheric, indoor air and greenhouse gas emissions. The materials and parameters of elements of the generator of these embodiments may change depending on the composition of the fluid (i.e., gas) entering the plasma field.

Some embodiments of the plasma generator 10 for indoor air sterilization require less voltage than other embodiments that are applied for greenhouse gas decomposition. In general, the composition of atmospheric/indoor air is 78% Nitrogen, 21% Oxygen, 0.93% Argon, and 0.04% Carbon Dioxide—the remainder being trace amounts. To create sufficient stable plasma to sterilize indoor air, some embodiments of the plasma generator 10 produce a minimum voltage, ranging from 3 kV-7.5 kV, based on bond energies and electron Volts required to separate Hydrogen—Oxygen bonds (1.23 eV), reforming into hydroxyl radicals (OH), hydrogen peroxide ($H_2O_2$), as well as sufficient energy to eradicate specific pathogens (i.e., viruses, bacteria, fungi, etc.).

In some of these embodiments, once the voltage range is established, the capacitance requirements of the plasma generator can be calculated. Some embodiments for indoor air sterilization are designed with a 2 mm plasma gap, 2 mm dielectric layer 14 with a minimum relative permittivity of 4. Some of these embodiments use borosilicate glass as the insulating layer, which includes a relative permittivity of 4.7 at 60 Hz and minimum dielectric strength of 30 kV/mm (to ensure there is no or reduced dielectric breakdown).

In some of these embodiments, once the voltage range is established, the capacitance requirements of the plasma generator can be calculated. Some embodiments for indoor air sterilization are designed with a 2 mm plasma gap, 2 mm dielectric layer 14 with a minimum relative permittivity of 25. Some of these embodiments use ceramic as the insulating layer, which includes a relative permittivity of 25 at 60 Hz and minimum dielectric strength of 24 kV/mm (to ensure there is no or reduced dielectric breakdown).

Some embodiments use a 6 cm×9 cm electrode 16*a*, 16*b* formed of aluminum, with a total area of 54 $cm^2$ per electrode. Total separation distance between electrodes 16*a*, 16*b* for some of these embodiments is 6 mm. Once standards are established, the electrical components necessary to convert inputted DC 12 V to the required AC 3 kV-7.5 kV can be determined. Based on the air flow requirements calculated using streamer discharge, length and width of electrode 16*a*, 16*b* and the plasma Gap 15, additional Plasma Gaps 15 can be added while maintaining the same voltage requirements. At such time that stable plasma is no longer generated due to the cumulative area (cm2) of the electrode 16*a*, 16*b* exceed the applied voltage, revisions can be made to the voltage, dielectric layers, and plasma Gap 15 parameters. All of the embodiments are intended to cover applications where any fluid is disposed in the Gap 15. For example, the fluid in the gap can be "atmospheric air" (such as in the context of the tables of FIG. 8 and FIG. 9, any other gas or gaseous material (including but not limited to products and byproducts of industrial or commercial processes, etc.), any fluid in liquid form, any slurry, etc. In fact, the fluid is not even limited to the before-mentioned fluids and is intended to cover any substance disposed in the Gap 15.

C. Variation of Embodiments

Embodiments are intended to include or otherwise cover any methods and apparatus for creating stable cold plasma. Some of these embodiments are directed to generating stable cold plasma under atmospheric conditions where ambient fluid and small biological particles enter and interact with the plasma. In some of these embodiments, some or all of the small biological particles are sterilized by interaction with the stable cold plasma. However, other embodiments generate stable cold plasma for interaction with other fluids, such as fluids that include various gas species and concentrations.

Some embodiments include or otherwise cover relatively small electrode plates (such as, for example, electrode plates that are defined by a width of 6 cm and length of 9 cm), where a first electrode may have a dielectric layer that is formed of insulating material, such as glass, on its bottom surface. A second electrode plate of approximately the same size as the first electrode plate (in some embodiments 6 cm×9 cm) may also have a dielectric layer on its top side formed of the same dielectric material as the dielectric layer of the first electrode. The stacking configurations of some of these embodiments may define a constant 6 mm separation between the first and second electrode plates.

In some of these embodiments, this 6 mm separation includes the two dielectric layers and a gap in which stable cold plasma is generated. In some of these embodiments that include the 6 mm separation between electrodes, the dielectric layer may be 2 mm thick on each electrode plate, resulting in a 2 mm gap in which plasma is generated. In some of these embodiments, the stable cold plasma is generated upon AC 5 kV being applied to the electrodes at 60 Hz.

Some other embodiments include or otherwise cover relatively large electrode plates (such as, for example, electrode plates that are defined by a width of 30 cm and length of 30 cm) in the same or similar configurations as described above regarding the relatively smaller (e.g., 6 cm×9 cm) electrode plates. Some of these embodiments that include relatively larger electrodes may be especially beneficial because they may generate a relatively larger volume of stable cold plasma and enable a relatively larger volume of fluid to flow through the gap.

More specifically, embodiments that also include a constant 6 mm separation between the first and second electrodes, where the thickness of each dielectric layer is 2 mm and the plasma gap is 2 mm, enable a relatively increased volume of plasma generated in the gap between the dielectric layers as well as a relatively increased volume of fluid flowing through the plasma gap. In these embodiments, relatively larger electrode plates may be beneficial because they increase the capacitance of the system, yet the applied voltage and frequency will remain the same as that used for relatively small plate configurations.

In some of these and other embodiments, the dielectric layer thickness may be less than 2 mm. For example, if the dielectric layers of these embodiments has a thickness of 1 mm or 1.5 mm, then the plasma gap will increase, assuming a fixed separation between electrodes. In some of these embodiments, this increased gap may cause a slight increase in capacitance, and the burning voltage may also increase due to a smaller dependence on the surface electron emission properties of the dielectric layer on both the first and second electrode plates. In some of these embodiments, these combined effects may cause the total amount of plasma generated through an AC cycle, as well as the volume of the plasma at any one time, to both decrease.

In some embodiments, if the plasma gap decreases due to a relatively thicker dielectric layer within the 6 mm separation between the first and second electrode plates (or for some other structural reason), then the capacitance and the burning voltage may decrease. In some of these embodiments, these effects may combine to allow for the total amount of plasma generated through an AC cycle as well as the volume of the plasma at any one time to both increase. These qualitative changes may be constant between different embodiments, such as the relatively small electrode plate configurations (e.g., 6 cm×9 cm) and the relatively large electrode plate configurations (e.g., 30 cm×30 cm). However, it is important to note that embodiments are not limited to these electrode plate sizes, and embodiments are intended to include or otherwise electrode plates of any size and shape that is usable to generate or help generate stable cold plasma.

In some embodiments, changes in relative permittivity, dielectric strength, and/or surface charge properties occurs if the insulating material of the dielectric layer changes, for example from glass to ceramic. This change may alter the capacitance of the system, the production rates of each chemical species in the plasma, and in some embodiments force a change to the applied voltage. However, in some of these embodiments, the frequency and gap size between each electrode plate, such as at an electrode separation of 6 mm, will remain constant. These changes are constant between relatively small electrode plate configurations (e.g., 6 cm×9 cm) and relatively large electrode plate configurations (e.g., 30 cm×30 cm).

In some embodiments, small electrode plates (e.g., 6 cm×9 cm) may be configured within larger (e.g., 12 cm×15 cm) plates that are made of the same material as the dielectric layer material. In some embodiments, large electrode plates (e.g., 30 cm×30 cm) may be configured within larger plates (e.g., 50 cm×50 cm) that are made of the same material as the dielectric layer material. Embodiments with these configurations include larger creepage areas.

D. Detailed Explanation

The plasma generator 10 of FIG. 1 is disclosed above at a high level and will be discussed in much more detail below.

Figure 2:
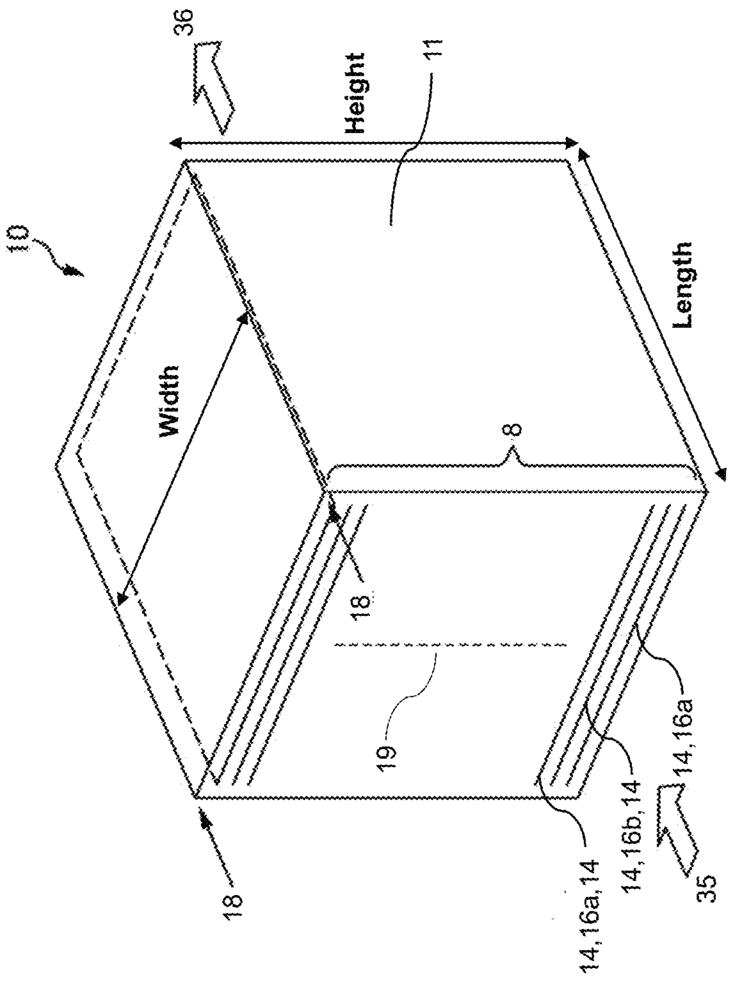
FIG. 2 is a perspective view of the plasma generator 10 of FIG. 1.

FIG. 2 is a perspective view of the plasma generator 10 of FIG. 1. FIG. 2 specially shows an exterior housing 11 of the plasma generator 10 that houses multiple stacked electrodes 16*a*, 16*b*, which are each laminated with a dielectric layer 14, and then vertically separated by gaps 15 from other electrodes 16*a*, 16*b* laminated with dielectric layers 14. These stacked layers extend vertically to a height 8 of the housing 11. Thus, the plasma generator 10 of FIG. 2 is formed in a rectangular parallelepiped shape having a rectangular plane as a whole.

As specifically shown in FIG. 2, each horizontal line represents an electrode 16*a*, 16*b*, which is laminated with either one or two dielectric layers 14. For example, the bottom horizontal line constitutes an electrode 16*a* laminated on its top surface with a dielectric layer 14, but not its bottom surface because it constitutes the lowermost layer. Similarly, the top horizontal line constitutes an electrode 16*a* laminated on its bottom surface with a dielectric layer 14, but not its top surface because it constitutes the topmost layer. However, the horizontal lines representing the layers in the middle, including the second lowermost layer, include an electrode 16*b* with both the top and bottom surfaces that are each laminated with a dielectric layer 14. Dashed line 19 in FIG. 2 represents multiple such layers extending vertically along the height 8 of the housing 11 in a vertically disposed central area of the housing 11. Each of the dielectric layers 14 are separated by a gap 15 such that many such gaps 15 are defined within the plasma generator 10.

An air inlet 35 enables air to enter a front end of the multiple stacked gaps 15, wherein plasma is generated when electrical power is applied to the electrodes 16*a*, 16*b*. Air is taken in from the front side of the plasma generator 10, passes through a plurality of flow paths defined by the gaps 15, and is exhausted from the rear of the plasma generator 10. In other words, each of the gaps 15 constitute air passages formed in the plasma generator 10, which in the embodiment of FIG. 2 is defined as a flat slit-shaped open area.

Stable cold plasma is generated within those gaps 15 so that the air contacts or otherwise communicates with the free ions and free electrons generated by the cold plasma, thereby causing molecules in the air to break down or otherwise be altered. Air with the broken down or altered molecules then exists the plasma generator 10 at the air outlet 36.

Figure 3:
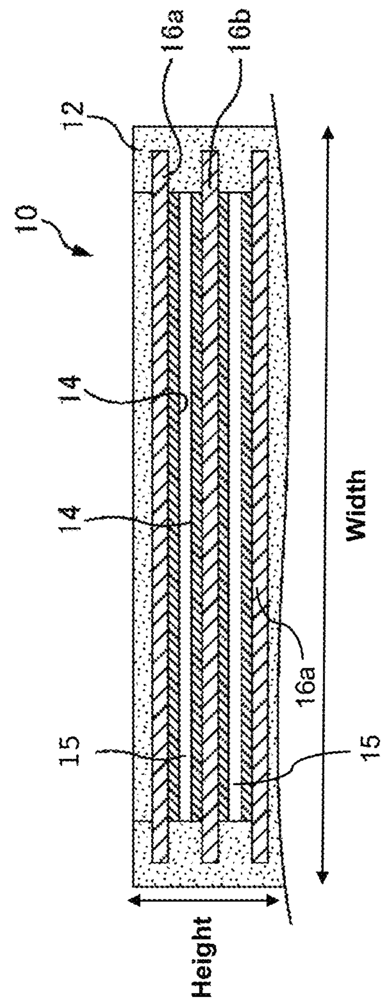
FIG. 3 is a partial cross-sectional view of the plasma generator 10 of FIG. 2.

FIG. 3 is a partial cross-sectional view of the plasma generator 10 of FIG. 2, which shows three such electrode/dielectric layers with two separate gaps 15 defined therebetween. As shown in FIG. 3, the top layer includes an electrode 16*a* that is laminated with a dielectric layer 14 on its bottom surface, which is then separated by a gap 15 from the adjacent layer disposed immediately there below, which itself includes an electrode 16*b* that is laminated by dielectric layers 14 on both its top and bottom surfaces.

The FIG. 3 embodiment shows the middle electrode 16*b* separated from each of its neighboring electrodes 16*a* (above and below) by two separate dielectric layers 14. In particular, a dielectric layer 14 is provided on both of its top and bottom surfaces, and a separate dielectric layer 14 on each of the neighboring electrodes 16*a*. However, embodiments are intended to cover structures where neighboring electrodes 16*a,* 16*b* are only separated by a single dielectric layer 14.

The electrodes 16*a,* 16*b* (with their attached dielectric layers 14) are held in place by a spacer 12 disposed at opposite width-wise ends. The spacer 12 holds the electrodes 16*a,* 16*b* in place so as to define the gaps 15, each extending vertically to a predetermined distance, between the dielectric layers 14. As shown in FIG. 3, the spacer 12 extends above, below, and to the side of side ends of each of the electrodes 16*a,* 16*b,* wherein the side ends are cantilevered beyond the dielectric layers 14 in the width-wise direction. The spacer 12 can also be disposed above the top and below the bottom of the stacks of electrodes/dielectric layers to further hold the structure together.

The spacer 12 can be formed of a single contiguous or unitary element, or alternatively can be formed by multiple elements. The spacer 12 is formed of an insulating material, similar or including (but not limited to) the materials from which the dielectric layer 14 are formed, and is intended to include any related art, currently known, or later developed material(s).

Figure 4:
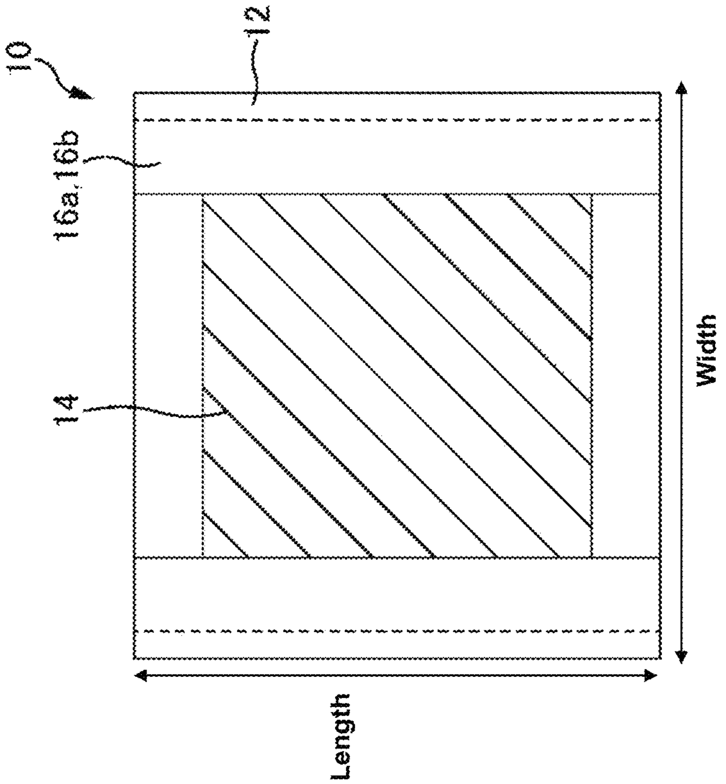
FIG. 4 is a top plan view of the plasma generator 10 of FIG. 2.

FIG. 4 is a top plan view of the plasma generator 10 of FIG. 2. As shown in FIG. 4, the spacer 12 is disposed at certain locations around the perimeter of the electrodes 16*a,* 16*b,* thereby holding them in place while also constituting an insulator. FIG. 4 specifically shows the spacer 12 extending around the sides of the electrodes 16*a,* 16*b*. Also as shown in FIG. 4, the dielectric layers 14 do not extend as far as the electrodes 16*a,* 16*b* in the widthwise direction, such that the face of each of the side ends of the dielectric layers 14 abuts the spacer 12.

In the embodiments of FIGS. 1-4, each of the electrodes 16*a,* 16*b* can be a metal or mesh plate in the shape of a thin sheet that is rectangular or square in top and bottom plan views, wherein the top and bottom surfaces are flat or planar. However, the electrodes 16*a,* 16*b* can be formed into any shape that may be beneficial for the application at issue. Thus, the width and length of each electrode 16*a,* 16*b* is each longer than its height. In some of these embodiments, the electrodes 16*a,* 16*b* are formed of an aluminum plate, but may be formed of any other suitable conductive related art, known, or later developed material, including but not limited to stainless-steel plate, silver, gold, magnesium alloy, etc.

Embodiments are intended to cover electrodes 16*a,* 16*b* of any size depending on application. It is beneficial to avoid bending of the electrodes 16*a,* 16*b*, such as that may result from widthwise interior section extend into the adjacent gap 15, which may occur based on mass and gravity and become particularly acute as the length of the electrode 16*a,* 16*b* increases. The size (including length) of the electrodes 16*a,* 16*b* can be increased by using stronger materials that resist such bending.

In the embodiments of FIGS. 1-4, each electrode is laminated, at least in part, with a dielectric layer 14 that is formed of a solid insulating resin, such as borosilicate glass, fiberglass, aluminum oxide, ceramics, Pantex glass, polyimide film, etc., allowing for high breakdown voltage. A creepage distance is located around each electrode 16*a,* 16*b,* allowing for high voltage to run through it. The size of the creepage distance as shown on FIG. 4 is based on industrial standards, such as those in the United States, Europe, or Japan.

In the embodiments of FIGS. 1-4, the dielectric layers 14 (insulating layers), at least in part, can be formed as a layer of glass, such as from the materials disclosed above or other materials. The dielectric insulating layer 14 operates to stabilize the plasma generated within the gap 15, and can include various other materials, such as quartz, ceramics, enamel, or similar materials. The thickness of each dielectric layer 14 can affect the stable cold plasma generation and so can fluctuate. For some embodiments, the thickness of each dielectric layer 14 produces a 2 mm gap 15 between adjacent dielectric layers 14.

In the embodiments of FIGS. 1-4, the dielectric layers 14 are provided on the surfaces of opposing electrodes 16*a,* 16*b,* and the dielectric layers 14 are supported so as to be parallel to each other while being separated by separators 12. The size of the separators 12 (which operate as spacing members) is determined by the thickness of electrodes 16*a* and 16*b,* dielectric layers 14, and gap 15. The separators 12 can be formed from any electrically insulating resin material, such as glass (similar to that used for the dielectric layers 14 as described above).

As discussed above, stable cold plasma can be generated within the gap 15 based on the following factors: 1) height of gap 15 separating the electrodes/dielectrics; 2) voltage of AC electrical power supplied to the electrodes 16*a*, 16*b;* 3) frequency of electrical power supplied to the electrodes 16*a,* 16*b;* and/or 4) structural characteristics of the plasma generator 10. Some of these structural factors that impact creating stable cold plasma include aspects of the dielectric layers 14, such as break voltage, i.e., the dielectric strength or kV per mm, and the relative permittivity. In some embodiments, creating stable cold plasma is enhanced by providing for a higher relative permittivity.

In the embodiments of FIGS. 1-4, the height of each gap 15 is set to be approximately 2 mm, and the thicknesses or height of each of the electrodes 16*a,* 16*b* is set to be approximately 2 mm. As schematically shown in FIG. 2, an appropriate number of gaps 15 (for example, about 30~40 layers) are provided in the height direction (height 8) of the plasma generator 10. However, any number of layers can be provided depending on the capacity required.

In some of the embodiments of FIGS. 1-4, the width of each gap 15 can be 100 mm-400 mm. However, it is especially beneficial for a width of the gap 15 to be 250 mm-350 mm, and still better if the width of the gap 15 is approximately 300 mm. However, in other embodiments, the width of the gap 15 can be reduced to 30 mm-90 mm. In those embodiments, it may be especially beneficial for the width of the gap 15 to be 45 mm-75 mm, and still better if the width of the gap 15 is approximately 60 mm. The depth of each gap 15 along the flow direction is approximately 300 mm. However, the size of each gap 15 can be modified as per application use, such as for the purpose of increasing the volume of fluid that can be processed while maintaining electricity levels that result in stable plasma generation.

As shown in FIG. 3, the separators 12 (formed of an electrically insulating resin material, similar to the glass used for the dielectric layer) can be formed to a height that exceeds the combined heights of the electrodes 16*a*, 16*b*, dielectric layers 14, and the gap 15. In other words, in some embodiments, the separators 12 extend adjacent side ends (in the widthwise direction) of the electrodes 16*a*, 16*b* and dielectric layers 14, and also above (in the height direction) cantilevered side ends of the electrodes 16*a*, 16*b*, which provides structural stability of the generator 10, especially in embodiments that include numerous stacked layers. For example, in an embodiment that includes two electrodes 16*a*, 16*b* that are each 2 mm in height, two dielectric layers 14 that are each 0.5 mm in height, and a gap that extends between the dielectric layers 14 to a height of 2 mm, it may be beneficial for the separator 12 to extend to a height exceeding 7 mm.

The size and number of dielectric layers 14 and electrodes 16*a*, 16*b* has a direct correlation to the voltage used. Thus, some embodiments increase the separator 12 size to handle higher voltages.

In the embodiments of FIGS. 1-4, stacking electrodes/dielectric layers helps create stable plasma generated in the gaps 15 defined therebetween. Further, the stacked design allows for more gaps 15 and thereby enables more fluid to pass through the plasma generator 10, which is beneficial for many applications. Embodiments are intended to include or otherwise cover any number of stacked electrode/dielectric layers separated from each other by gaps 15, including but not limited to 100 layers, 11 layers, etc. For example, some embodiments include stacked units with 11 electrodes 16*a*, 16*b*, resulting in 10 gaps 15 in which plasma is generated. However, it may be beneficial to provide enough electrodes 16*a*, 16*b* to define 20 gaps 15 in which stable cold plasma is generated.

In the embodiments of FIGS. 1-4, efficiencies of plasma generation are the same or substantially the same regardless of how much fluid is processed through the gaps 15 of the plasma generator 10. However, effectiveness of the plasma generation does change and is affected based on the type of fluid passing through the plasma generator.

In the embodiments of FIGS. 1-4, applying a predetermined AC voltage at a predetermined frequency between the electrodes 16*a*, 16*b* generates cold plasma in the gaps 15 between the dielectric layers 14, which is based on the dielectric barrier discharge induced in the plasma gap 15. This acts to ionize $CO_2$, for example, contained in air, disposed in the gap 15 and in contact with the plasma, to separate the carbon atoms and oxygen atoms. Specifically, a $CO_2$ molecule receiving energy from the plasma ionizes into a positively charged carbon atom (hereinafter "C+"), which has lost electrons in the outermost shell, and a negatively charged oxygen atom (hereinafter "O−"), which has received covalent electrons from the carbon atom. Ultimately, the ionized C+ and O− favor being recombined and returning to stable $CO_2$, and so a separation unit 21 described in the following section is provided adjacent to the downstream side of the plasma generator 10 to isolate the ionized C+ and O− before they naturally recombine.

Cold plasma acts on air and water vapor (i.e., fluid) to generate reactive oxygen species including various radicals, such as singlet oxygen (1 $O_2$), ozone ($O_3$), hydroxyl radical (OH), superoxide anion radical ($O_2$—), hydroperoxyl radical ($HO_2$) and hydrogen peroxide ($H_2O_2$). The fluid passing through each gap 15 of the plasma generator 10 flows while being in contact with the generated plasma by continuously spreading in each planar shaped gap 15. Microorganisms, such as viruses and bacteria, contained in the surrounding air sucked into each gap 15 are very quickly destroyed, such as within microseconds, by contacting the cold plasma. A mixture of a multi-plasma gas containing the reactive oxygen species inactivates the viruses and sterilizes the microorganisms. Thus, the plasma generator operates to effectively sterilize the ambient air entering the gaps 15.

Figure 5:
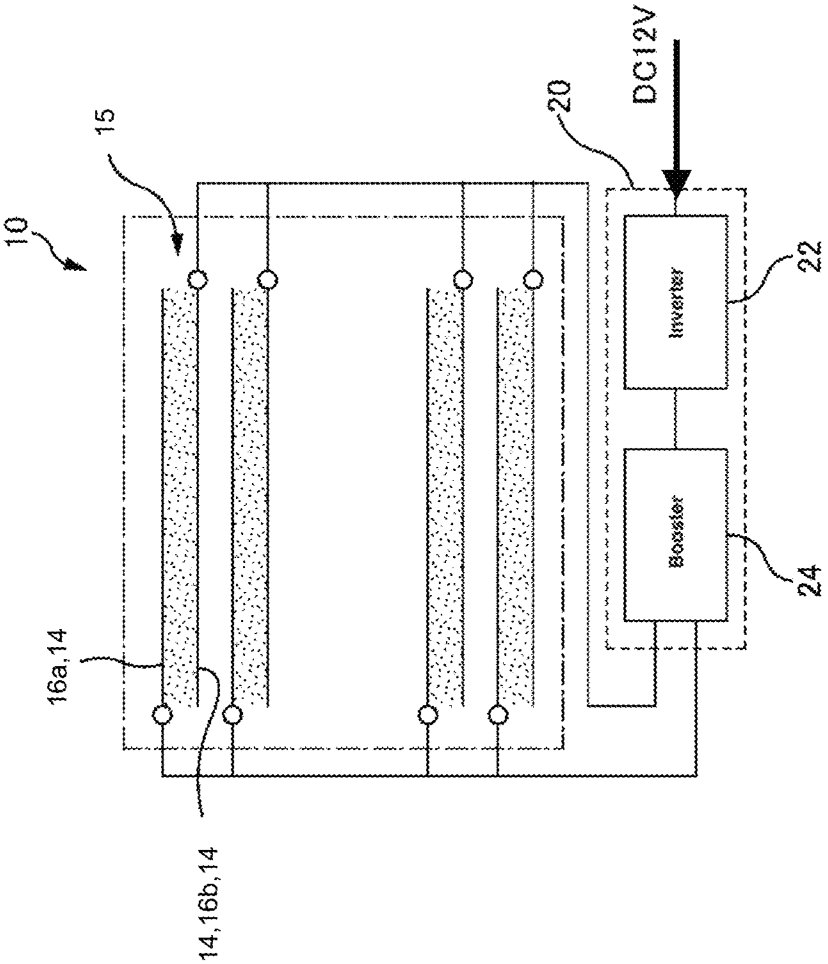
FIG. 5 is a schematic of an exemplary control circuit for the plasma generator 10 of FIG. 2.

FIG. 5 is a schematic of an exemplary control circuit for the plasma generator 10 of FIG. 2. As shown in FIG. 5, a power supply 20 supplies AC electrical power at a predetermined voltage and frequency to the electrodes to generate cold plasma within the gaps 15. The power supply includes and is intended to cover any related art, known, or later developed equipment for performing the above operation.

The power supply includes an inverter 22 and a booster 24, which is connected to each electrode 16*a*, 16*b*. DC 12 V is input to the inverter 22 of the plasma power supply unit 20 from an external power source. The inverter 22 outputs an AC voltage controlled in accordance with the input DC voltage and supplies it to the booster 24. The inverter 22 is sufficient for controlling the power, implementing the control method, the type of the switching element, etc.

Thus, the inverter 22 outputs an AC voltage corresponding to the input DC voltage, and more specifically an AC voltage that is proportional to the input voltage. For example, 1 kV AC is outputted if 1 V DC is applied, and 9 kV AC is outputted if 9 V DC is applied. In order to generate stable cold plasma, the output voltage needs to be controlled based on certain structural parameters of the plasma generator 10, such as the distance between the electrodes 16*a*, 16*b*, the material from which the electrodes are formed, the plane size and the thickness of the electrodes 16*a*, 16*b*. The AC frequency may be appropriately determined.

In some embodiments, the inverter 22 converts DC 12V to AC33.3V and transmits this voltage to the booster 24. The control method used to apply voltage to the electrodes 16*a*, 16*b* to maintain stable barrier discharge, and the amount of voltage sent to the booster, is controlled by the amplitude of the inverter output. A switching element for the separation unit 21 (described below) uses a Field Effect Transfer (FET) and is built into the inverter. The booster 24 uses a rate of 150× to convert the AC33.3V received from inverter to AC 15 kV.

In some embodiments, the inverter 22 converts DC 12V to AC 20V-AC 100V and transmits this voltage to the booster 24. The booster can have a predetermined rate of 150× and be capable of converting AC 20V-AC 100V to AC 3 kV-15 kV. It may be beneficial to boost AC 33.33V to AC 5 kV for stable cold plasma generation. The composition of the gas passing through the plasma Gap 15 may affect the voltage that is relevant or required for the stable cold plasma generation. In some applications, such as disinfecting and/or sterilizing, less voltage may be necessary, such as AC 5 kV, but in other applications, such as decomposing gases, higher voltage may be necessary, such as AC 7.5 kV-10 kV.

However, embodiments are intended to cover other voltages and voltage ranges as discussed in detail below. For example, 5 kV-10 kV may be especially beneficial, and 7.5 kV may be even more beneficial. Further, in some embodiments where ozone is a concern, the voltage levels may be beneficial at 3 kV-7 kV. However, 5 kV may be even more beneficial in this context.

Although barrier discharge is used in the plasma generator 10, discharge does not occur when the voltage between the electrodes 16*a*, 16*b* is low. When the voltage between the electrodes 16*a*, 16*b* is high, it shifts to spark discharge or arc discharge, which leads to a decrease in the generation efficiency of active species by the plasma and damage of the electrodes 16*a*, 16*b* due to the concentration of discharge in a specific place.

In the present embodiments, the stable barrier discharge is maintained by controlling the AC voltage applied between the electrodes 16*a*, 16*b*. Thus, the generation of plasma can be stably and continuously performed. Further, by controlling an AC voltage applied between the electrodes, a multi-plasma gas containing active oxygen species is efficiently generated while suppressing generation of harmful ozone ($O_3$).

Voltage levels that produce stable barrier discharge range from 3 kV to 9 kV, although 5 kV may be more advantageous. Due to electrochemical properties, the amount of ozone generated is controlled by voltage. Low voltage 5 kV, for example, generates lower ozone concentrations and the higher voltage 10 kV, for example, generates higher amounts of ozone. The applicable voltage levels may increase to allow for additional plasma generators 10 to be stacked to allow for stable plasma generation. In some embodiments where ozone is not a concern, such as for $CO_2$ decomposition, the voltage levels that may be beneficial are 3 kV-15 kV. However, 5 kV-10 kV may be especially beneficial, and 7.5 kV may be even more beneficial. Further, in some embodiments where ozone is a concern, the voltage levels may be beneficial at 3 kV-7.5 kV. However, 5 kV may be even more beneficial.

The frequency of the electrical power supplied to the electrodes is also relevant to the plasma generation. The frequency is determined by the inverter 22 and can range from 30-50 Khz. However, it is advantageous for some embodiments for the frequency to be 50 Hz for Japan and 60 Hz for the United States. At 50 Hz, frequency equals 20 ms and streamer discharge at 10 ms. At 60 Hz, frequency equals 16.67 ms and streamer discharge at 8.33 ms.

As discussed above, multiple stacked layers of electrodes 16*a*, 16*b* and dielectric layers 14 can be used to scale each plasma generator 10, and in fact separate plasma generators 10 can be stacked such as by being vertically aligned. The voltage used to power multiple stacked plasma generators 10 can be augmented by the booster 24 and the inverter 22.

Thus, as discussed above, creating a stable cold plasma depends on a combination of elements, including voltage, frequency, composition of electrodes and dielectric material, structure, size, spacing, creepage distance, and processing of electrodes. However, the selected voltage and frequency of the electrical power supplied to the electrodes 16*a*, 16*b* and the dielectric strength and relative permittivity are especially important to generate stable cold plasma.

Tables in FIG. 8 and FIG. 9 describe specific parameters of the plasma generator. Each table describes specific examples of parameters that may be found in exemplary embodiments. Each table references parameters depicted in configurations described in FIGS. 1-7. However, it is important to note that the parameters disclosed therein are provided merely for exemplary purposes and are not intended to be limiting in any way. In fact, embodiments are intended to include or otherwise cover plasma generators that include any parameters to create or facilitate the creation of stable cold plasma in atmospheric air. Atmospheric air is defined here to be gas composed of the same relative constituents, temperatures, and pressures as the average atmospheric conditions in the location of the device, with humidity that varies naturally.

The tables shown in FIG. 8 and FIG. 9 convey the large changes in the plasma generation process that stem from minute changes to the configuration and other parameters. Each table references a single stacked layer configuration of the plasma generator 10 found in FIGS. 1-7, where there is a first electrode 16*a* and second electrode 16*b*, each with a dielectric layer 14 on the surface that faces the gap 15 created between the two electrodes. However, the parameters in each table in FIG. 8 and FIG. 9 can be multiplied for each layer present in a particular embodiment that contains multiple or stacked plasma generating layers. The optimization of the plasma device for the formation of free radicals and other reactive species is shown to depend on minute changes in the parameters. These parameters are dependent on constants such as the space between each layered electrode plates, the thickness of the dielectric material and the dimensions of the plasma gap. Some of these constants are changed between FIG. 8 and FIG. 9 to show some of the changes to the properties of the system due to the changes in the configuration and materials of the device.

Some parameters are well defined and described in explicit units, while other parameters are difficult to measure. Parameters that are difficult to measure are described in the tables using an arbitrary qualitative scale, or a scale used to convey qualitative changes.

FIG. 8 is a table of different parameters for a plasma generator with dielectric layers formed of borosilicate glass. Every column alternates between parameters for an exemplary small electrode configuration (6 cm×9 cm) and parameters for an exemplary large electrode configuration (30 cm×30 cm), as noted in the top row. However, as indicated previously herein, embodiments are intended to include or otherwise cover other electrode sizes.

The first parameter, starting from Row 1, is "Electrode Material". The electrode is the circuit element that allows current to pass through its volume to its surface, but the electrons stay confined to the surface and cannot pass through the dielectric material adjoining the surface of the electrode directly opposite the incoming current. This parameter is constant through all variations in the table and between FIG. 8 and FIG. 9, with the single value of "Aluminum".

Row 2 is "Electrode Gap", which describes the distance between the surfaces of two layered electrodes in millimeters (mm). This parameter is a constant and thus remains unchanged through all variations in the table and has a single value of "6 mm"

Row 3 is "Dielectric Layer Material", which describes the material that constitutes the dielectric layers of the plasma generator. In this embodiment, the dielectric layer is on each stacked electrode. The dielectric material is defined to be a material that can inherently polarize in the presence of an external electric field, thus reducing the electric field within. The charges within the dielectric layer are bound and thus its purpose is to prevent any current from passing through its bulk. This then limits the amount of current that passes through the fluid between the dielectric surfaces, preventing the current from heating the fluid far above room temperature. This parameter also remains unchanged through all variations in the table and has the single value of "Borosilicate Glass".

Row 4 is "Dielectric Thickness", which is the thickness of each of the two dielectric layers between the electrodes in millimeters. This parameter increases as the columns progress to the right of the table. This parameter is an independent variable, and the dependent parameters depend on its value. This means that this is the only parameter that is actively being varied in the chart and all changes of other parameters are completely dependent on the changes of the independent variable "Dielectric Thickness".

Row 5 is "Relative Permittivity", which is the dimensionless ability of the dielectric layer to reduce an externally applied electric field within the dielectric material—in other words its ability to polarize in an external electric field. The relative permittivity of a vacuum is assumed to be 1, and all other relative permittivity values are greater than this value. This parameter depends on the "Dielectric Layer Material" row and the "Frequency" row, and thus remains unchanged through all variations in the table because the dielectric layer and frequency are constant, having the single value of "4.7".

Row 6 is "Dielectric Strength", which is the electric field threshold that initiates transition from insulator (i.e., dielectric layer 14) to conductor (i.e., electrode 16*a*, 16*b*) and allows significant electric current to pass through. An insulator is a material with the ability to prevent electric charge carriers from passing through at a certain electric field (i.e., dielectric layer 14), whereas a conductor is a material that can allow large amounts of charge carriers to pass through at the same voltage (i.e., electrode 16*a*, 16*b*). For high voltage conditions, a higher dielectric strength is desirable so that charge is allowed to build on or over the surfaces of the dielectric layers and does not pass through the dielectric material. If significant electric current were to pass through the dielectric layer, the purpose of the dielectric would become obsolete, because the current through the fluid in the plasma gap 15 would no longer be limited. This would cause significant heating of the fluid and power consumption would increase, vastly decreasing the efficiency of the device. This parameter depends on the material used for the "Dielectric Layer Material" row and thus remains unchanged through all variations in the table and has the single value of "30 kV/mm".

Row 7 is "Plasma Gap", which is the distance in millimeters between the two dielectric layers, and the region that contains the gas/fluid and in which the stable cold plasma is generated i.e., plasma gap 15. This parameter decreases as from left to right in the table due to the dielectric layer increasing in thickness.

Row 8 is "Frequency", which is the frequency in Hertz (Hz) of the alternating current (AC) applied to the electrodes that are connected to the plasma power supply 20. This parameter remains unchanged through all variations in the table and has the single value of "60 Hz".

Row 9 is "Applied Voltage", which is the RMS (root-mean-square) value in kilovolts (kV) of the AC voltage applied to at least one of the electrodes connected to the plasma power supply 20. This parameter remains unchanged through all variations in the table and has the single value of "5 kV".

Row 10 is "Streamer Discharge", which is the amount of time during a bipolar wave pulse during which plasma micro discharges form within the gas/fluid, or the time during which the gap between the dielectric layer surfaces is at the absolute value of burning voltage, which is another parameter that is described below. A bipolar wave pulse is also known as a single alternating current cycle. Micro discharges are the individual filaments that allow current to pass between the surfaces of the dielectrics and are the actual plasma forming regions in the gas/fluid. Micro discharges occur on the order of nanoseconds.

The voltage between the dielectric layer surfaces, in the plasma/fluid gap region, is known as the plasma gap voltage, which is different from the applied voltage. The plasma gap voltage is the mechanism by which the streamer discharge and other parameters vary, and the concept can be used to justify qualitative changes in those parameters. The existence of a micro discharge is dependent on the value of the plasma gap voltage at a particular moment of time: if the plasma gap voltage is too low, the micro discharges cannot exist, and if the plasma gap voltage reaches the critical value of the burning voltage, the micro discharges can form plasma. The plasma gap voltage depends on the charges built up on the electrode surfaces and on the charges built up on the dielectric layer surfaces. Once the charge buildup on the electrodes creates a plasma gap voltage during the rising portion of the AC cycle that is equal to a threshold value known as the burning voltage (described below), micro discharges carry small amounts of charge from one dielectric layer surface to the other.

The charge carried by a micro discharge creates a negative voltage that brings the plasma gap voltage below the value of the burning voltage. This process happens every time the plasma gap voltage momentarily rises above the burning voltage. There is also subtle variability in the surface charges on the surfaces of the dielectric layers, so a micro discharge in one location in the plasma gap 15 will not significantly influence the plasma gap voltage in another location in the plasma gap 15. Thus, there could be many micro discharges occurring at once that all work to keep the average plasma gap voltage at the value of the burning voltage through the existence of the micro discharges. Using an arbitrary qualitative scale, the value of the streamer discharge parameter increases from left to right on the table for small electrodes, and then increases on a separate scale for large electrodes. However, when changing from a small electrode to a large electrode while keeping the independent variable of dielectric layer thickness constant, the value of this parameter decreases. In other words, the amount of time during which the absolute value of the average plasma gap voltage between the dielectric layers surfaces is at the value of burning voltage increases as the thickness of the dielectric layer is increased and the plasma gap distance (height if electrodes are stacked vertically) is decreased. The reason for this might be that the streamer discharge roughly follows the changes in capacitance (described below). A lower capacitance will lead to a faster buildup of charge and thus a larger plasma gap voltage. The time that the plasma gap voltage is at the burning voltage will then increase, leading to an increase in the value of this parameter.

Row 11 is "Capacitance", which is the amount of surface charge that can be stored on the electrode plates divided by the voltage difference between the electrode plates. For multiple dielectric layers (the dielectric layers and the gas/fluid in the plasma gap, which also has dielectric properties), the following formula is used:

$$C = \epsilon A \frac{\kappa 1 \kappa 2}{\kappa 2 d1 + \kappa 1 d2}$$

where C is the capacitance, ε is the vacuum permittivity constant, A is the surface area of one of the electrode plates, κ1 is the relative permittivity of the dielectric layer, κ2 is the relative permittivity of the gas/fluid in the plasma gap, d1 is the combined thickness of both of the dielectric layers, and d2 is the plasma gap distance between the dielectric layers.

The capacitance in the context of the disclosed embodiments represents the amount of time it takes for the electrode plates to build up electric charge, which is the mechanism responsible for inducing an electric field within the plasma gap. In an AC cycle, this also represents how close the plasma gap voltage within the plasma gap is to the applied voltage. Higher values of capacitance might decrease the time and the amount of plasma in the gap. The capacitance increases when changing from a small electrode configuration to a large electrode configuration with all other parameters remaining constant. The capacitance increases then the thickness of the dielectric layer is increased, represented in the table from left to right in the table.

Row 12 is "Impedance", which is the amount of resistance to the flow of alternating current into and out of the electrodes. The impedance inversely correlates with the induced current, with lower impedance inducing greater current. This relationship can be demonstrated by Ohm's law for AC circuits, where impedance is equal to the root mean square (RMS) value of applied voltage divided by the RMS value of induced current. In the calculation below, resistive effects are ignored and only capacitive effects are considered, because capacitive effects dominate.

In this case, the impedance is equal to the magnitude of the capacitive reactance (a well-known electrical engineering term that describes the amount of electrical energy an AC circuit can store in a capacitor), with the following formula:

$$Z = \frac{1}{2\pi fC}$$

where Z is the impedance, f is the frequency of the applied alternating current, and C is the capacitance of the device. The impedance of the plasma generator decreases if changing from a relatively small electrode configuration to a relatively large electrode configuration. The impedance of the plasma generator increases if the thickness of the dielectric layer is increased, represented in the table from left to right in the table.

Row 13 is "Peak Reduced Electric Field", which is the peak electric field divided by the number density of the fluid. This parameter is described in Townsend units (Td). The approximate plasma gap voltage is calculated to be the applied voltage divided by 0.707 (in order to convert root mean square applied voltage to peak applied voltage), and thus the peak reduced electric field is the peak plasma gap voltage divided by the distance between the electrodes (i.e., 6 mm in the current embodiment), which is the plasma gap plus the thickness of both dielectric layers. The following formula is used to calculate the peak reduced electric field:

$$E/N = \frac{\mathrm{V}}{(0.707)d\,n_0} \times \left(10^{21}\,\mathrm{V}^{-1} m^{-2}\right)$$

where E/N is the approximate peak reduced electric field, V is the RMS applied voltage, d is the electrode distance, $n_0$ is the Loschmidt constant, equal to $2.7\times10^{25}$ $m^{-3}$, and the factor of $10^{21}$ is used to convert to Townsend units.

The true plasma gap voltage is lower than the applied plasma gap voltage applied to the electrodes and changes due to capacitive effects. This parameter depends on the "Electrode Gap" row, and the "Applied Voltage" row and remains unchanged through all variations in the table because all of these parameters remain constant, having the single value of "43.82 Td".

Row 14 is "Ignition Voltage", which is the voltage between the electrodes that initiates the very first micro discharge in the plasma gap in the operation of the entire device. This parameter depends mainly on the surface properties of the dielectric layer material, the distance between the dielectric layers, and the composition of the gas/fluid in the plasma gap. The ignition voltage can also depend on the amount of time the device has been turned off between operations, decreasing with smaller breaks in operation. Using an arbitrary qualitative scale, the value of this parameter decreases from left to right in the table, every other column. In other words, the ignition voltage decreases when the thickness of the dielectric layer is increased.

Row 15 is "Burning Voltage", which is the voltage between the electrodes that initiates sustained micro discharges after many AC cycles. This voltage is an asymptotic property, meaning the voltage that initiates micro discharges will lower from the ignition voltage and approach the burning voltage over many AC cycles. Using an arbitrary qualitative scale and comparing it to the "Ignition Voltage" row, the value of this parameter is always lower than that of the ignition voltage and decreases from left to right in the table, every other column. In other words, the burning voltage also decreases when the thickness of the dielectric layer is increased.

Row 16 is "Micro Discharge Number", which is the number of micro discharges present in the plasma gap region at any one time. Because micro discharges have a filamentary volumetric shape and all are the same size, the number of micro discharges is nearly synonymous with the momentary volume of plasma present in the plasma gap region. Using an arbitrary qualitative scale, the value of this parameter increases when traveling from left to right in the table, but at separate scales for small electrodes and large electrodes.

When changing from a small electrode to a large electrode while keeping the independent variable of dielectric layer thickness constant, the value of this parameter also increases. In other words, the momentary plasma volume increases when the thickness of the dielectric layer is increased or when the surface area of the electrodes is increased. The reason for this might be related to the decrease in burning voltage; if the applied voltage remains constant, the burning voltage threshold occurs earlier in the AC cycle where the slope of the plasma gap voltage is greater. This will cause the number of micro discharges to increase in order to more quickly cancel the rising plasma gap voltage and keep it at the value of the burning voltage.

However, in some configurations, the decrease in plasma gap distance will decrease the length of each micro discharge, which might also decrease the volume of the micro discharges to a small degree. This might lead to either a smaller increase in the micro-discharge number or a decrease in micro-discharge number when increasing the thickness of the dielectric layer.

In some embodiments, there can be one or two dielectric layers between each pair of electrodes, yielding good results when there are two dielectric layers between each pair of electrodes. The number of electrodes can also vary, wherein the horizontally aligned electrodes are stacked vertically with dielectric layers and fluid gaps between every stacked electrode such that first and second electrodes serve as top and bottom electrodes to adjoin one plasma gap in a stack of electrodes and dielectric layers to create multiple plasma gaps. The number of electrodes can be configured to be between two and fifty-one, where the number of gaps between electrodes can be between one and fifty, yielding good results with the number of fluid gaps between five and twenty, and still further at ten.

The stacking process described above changes some of the parameters in the tables. The capacitance scales linearly with the number of plasma gaps, so for an arrangement of five plasma gaps, the capacitance is equal to that of a single plasma gap multiplied by five. This increase in capacitance would clearly decrease the impedance, using the formula given in the embodiments above. This would also decrease the speed of charge buildup on the electrode plate surfaces, and thus lowering the plasma gap voltage between the plates. The lower plasma gap voltage would then decrease the amount of time that the plasma can be held at the burning voltage, decreasing the streamer discharge.

FIG. 9 is a table of different parameters for a plasma generator with dielectric layers formed of ceramic. The leftmost column identifies the parameter that is assigned to the values in the same row. Every column alternates between an exemplary small electrode configuration (6 cm×9 cm) and an exemplary large electrode configuration (30 cm×30 cm), demonstrated by the top row. However, as indicated previously herein, embodiments are intended to include or otherwise cover other electrode sizes.

The first parameter, starting from Row 1, is "Electrode Material". The electrode is the circuit element that allows current to pass through its volume to its surface, but the electrons stay confined to the surface and cannot pass through the dielectric material adjoining the surface of the electrode directly opposite the incoming current. This parameter is constant through all variations in the table and between FIG. 8 and FIG. 9, with the single value of "Aluminum".

Row 2 is "Electrode Gap", which describes the distance between the surfaces of two layered electrodes in millimeters (mm). This parameter is a constant and thus remains unchanged through all variations in the table and has a single value of "6 mm".

Row 3 is "Dielectric Layer Material", which describes the material that constitutes the dielectric layers of the plasma generator. In this embodiment, the dielectric layer is on each stacked electrode. The dielectric material is defined to be a material that can inherently polarize in the presence of an external electric field, thus reducing the electric field within. The charges within the dielectric layer are bound and thus its purpose is to prevent any current from passing through its bulk. This then limits the amount of current that passes through the fluid between the dielectric surfaces, preventing the current from heating the fluid far above room temperature. This parameter also remains unchanged through all variations in the table and has the single value of "Ceramic".

Row 4 is "Dielectric Thickness", which is the thickness of each of the two dielectric layers between the electrodes in millimeters. This parameter increases as the columns progress to the right of the table. This parameter is an independent variable, and the dependent parameters depend on its value. This means that this is the only parameter that is actively being varied in the chart and all changes of other parameters are completely dependent on the changes of the independent variable "Dielectric Thickness".

Row 5 is "Relative Permittivity", which is the dimensionless ability of the dielectric layer to reduce an externally applied electric field within the dielectric material—in other words its ability to polarize in an external electric field. The relative permittivity of a vacuum is assumed to be 1, and all other relative permittivity values are greater than this value. This parameter depends on the "Dielectric Layer Material" row and the "Frequency" row, and thus remains unchanged through all variations in the table because the dielectric layer and frequency are constant, having the single value of "25".

Row 6 is "Dielectric Strength", which is the electric field threshold that initiates transition from insulator (i.e., dielectric layer 14) to conductor (i.e., electrode 16*a*, 16*b*) and allows significant electric current to pass through. An insulator is a material with the ability to prevent electric charge carriers from passing through at a certain electric field (i.e., dielectric layer 14), whereas a conductor is a material that can allow large amounts of charge carriers to pass through at the same voltage (i.e., electrode 16*a*, 16*b*). For high voltage conditions, a higher dielectric strength is desirable so that charge is allowed to build on or over the surfaces of the dielectric layers and does not pass through the dielectric material. If significant electric current were to pass through the dielectric layer, the purpose of the dielectric would become obsolete, because the current through the fluid in the plasma gap 15 would no longer be limited. This would cause significant heating of the fluid and power consumption would increase, vastly decreasing the efficiency of the device. This parameter depends on the material used for the "Dielectric Material Layer" row and thus remains unchanged through all variations in the table and has the single value of "24 kV/mm".

Row 7 is "Plasma Gap", which is the distance in millimeters between the two dielectric layers, and the region that contains the gas/fluid and in which the stable cold plasma is generated i.e., plasma gap 15. This parameter decreases as from left to right in the table due to the dielectric layer increasing in thickness.

Row 8 is "Frequency", which is the frequency in Hertz (Hz) of the alternating current (AC) applied to the electrodes that are connected to the plasma power supply 20. This parameter remains unchanged through all variations in the table and has the single value of "60 Hz".

Row 9 is "Applied Voltage", which is the RMS (root-mean-square) value in kilovolts (kV) of the AC voltage applied to at least one of the electrodes connected to the plasma power supply 20. This parameter remains unchanged through all variations in the table and has the single value of "5 kV".

Row 10 is "Streamer Discharge", which is the amount of time during a bipolar wave pulse during which plasma micro discharges form within the gas/fluid, or the time during which the gap between the dielectric layer surfaces is at the absolute value of burning voltage, which is another parameter that is described below. A bipolar wave pulse is also known as a single alternating current cycle. Micro discharges are the individual filaments that allow current to pass between the surfaces of the dielectrics and are the actual plasma forming regions in the gas/fluid. Micro discharges occur on the order of nanoseconds.

The voltage between the dielectric layer surfaces, in the plasma/fluid gap region, is known as the plasma gap voltage, which is different from the applied voltage. The plasma gap voltage is the mechanism by which the streamer discharge and other parameters vary, and the concept can be used to justify qualitative changes in those parameters. The existence of a micro discharge is dependent on the value of the plasma gap voltage at a particular moment of time: if the plasma gap voltage is too low, the micro discharges cannot exist, and if the plasma gap voltage reaches the critical value of the burning voltage, the micro discharges can form plasma. The plasma gap voltage depends on the charges built up on the electrode surfaces and on the charges built up on the dielectric layer surfaces.

Once the charge buildup on the electrodes creates a plasma gap voltage during the rising portion of the AC cycle that is equal to a threshold value known as the burning voltage (described below), micro discharges carry small amounts of charge from one dielectric layer surface to the other. The charge carried by a micro discharge creates a negative voltage that brings the plasma gap voltage below the value of the burning voltage. This process happens every time the plasma gap voltage momentarily rises above the burning voltage. There is also subtle variability in the surface charges on the surfaces of the dielectric layers, so a micro discharge in one location in the plasma gap 15 will not significantly influence the plasma gap voltage in another location in the plasma gap 15. Thus, there could be many micro discharges occurring at once that all work to keep the average plasma gap voltage at the value of the burning voltage through the existence of the micro discharges.

Using an arbitrary qualitative scale, the value of the streamer discharge parameter increases from left to right on the table for small electrodes, and then increases on a separate scale for large electrodes. However, when changing from a small electrode to a large electrode while keeping the independent variable of dielectric layer thickness constant, the value of this parameter decreases. In other words, the amount of time during which the absolute value of the average plasma gap voltage between the dielectric layers surfaces is at the value of burning voltage increases as the thickness of the dielectric layer is increased and the plasma gap distance (height if electrodes are stacked vertically) is decreased. The reason for this might be that the streamer discharge roughly follows the changes in capacitance (described below). A lower capacitance will lead to a faster buildup of charge and thus a larger plasma gap voltage. The time that the plasma gap voltage is at the burning voltage will then increase, leading to an increase in the value of this parameter.

Row 11 is "Capacitance", which is the amount of surface charge that can be stored on the electrode plates divided by the voltage difference between the electrode plates. For multiple dielectric layers (the dielectric layers and the gas/fluid in the plasma gap, which also has dielectric properties), the following formula is used:

$$C = \epsilon A \frac{\kappa 1 \kappa 2}{\kappa 2 d1 + \kappa 1 d2}$$

where C is the capacitance, ε is the vacuum permittivity constant, A is the surface area of one of the electrode plates, κ1 is the relative permittivity of the dielectric layer, κ2 is the relative permittivity of the gas/fluid in the plasma gap, d1 is the combined thickness of both dielectric layers, and d2 is the plasma gap distance between the dielectric layers.

The capacitance in the context of the disclosed embodiments represents the amount of time it takes for the electrode plates to build up electric charge, which is the mechanism responsible for inducing an electric field within the plasma gap. In an AC cycle, this also represents how close the plasma gap voltage within the plasma gap is to the applied voltage. Higher values of capacitance might decrease the time and the amount of plasma in the gap. The capacitance increases when changing from a small electrode configuration to a large electrode configuration with all other parameters remaining constant. The capacitance increases then the thickness of the dielectric layer is increased, represented in the table from left to right in the table.

Row 12 is "Impedance", which is the amount of resistance to the flow of alternating current into and out of the electrodes. The impedance inversely correlates with the induced current, with lower impedance inducing greater current. This relationship can be demonstrated by Ohm's law for AC circuits, where impedance is equal to the root mean square (RMS) value of applied voltage divided by the RMS value of induced current. In the calculation below, resistive effects are ignored, and only capacitive effects are considered, because capacitive effects dominate.

In this case, the impedance is equal to the magnitude of the capacitive reactance (a well-known electrical engineering term that describes the amount of electrical energy an AC circuit can store in a capacitor), with the following formula $$Z = \frac{1}{2\pi f C}$$

where Z is the impedance, f is the frequency of the applied alternating current, and C is the capacitance of the device. The impedance of the plasma generator decreases if changing from a relatively small electrode configuration to a relatively large electrode configuration. The impedance of the plasma generator decreases if the thickness of the dielectric layer is increased, represented in the table from left to right in the table.

Row 13 is "Peak Reduced Electric Field", which is the peak electric field divided by the number density of the fluid. This parameter is described in Townsend units (Td). The approximate plasma gap voltage is calculated to be the applied voltage divided by 0.707 (in order to convert root mean square voltage to peak voltage), and thus the peak electric field is the plasma gap voltage divided by the distance between the electrodes (i.e., 6 mm in the current embodiment), which is the plasma gap plus the thickness of both dielectric layers. The following formula is used to calculate the peak reduced electric field:

$$E/N = \frac{V}{(0.707) d\, n_0} \times \left(10^{21} \mathrm{V}^{-1} m^{-2}\right)$$

where E/N is the approximate peak reduced electric field, V is the RMS applied voltage, d is the electrode distance, $n_0$ is the Loschmidt constant, equal to $2.7\times10^{25}$ $m^{-3}$, and the factor of $10^{21}$ is used to convert to Townsend units.

The true plasma gap voltage is lower than the applied voltage that is applied to the electrodes and changes due to capacitive effects. This parameter depends on the "Electrode Gap" row, and the "Applied Voltage" row and remains unchanged through all variations in the table because all of these parameters remain constant, having the single value of "43.82 Td".

Row 14 is "Ignition Voltage", which is the voltage between the electrodes that initiates the very first micro discharge in the plasma gap in the operation of the entire device. This parameter depends mainly on the surface properties of the dielectric layer material, the distance between the dielectric layers, and the composition of the gas/fluid in the plasma gap. The ignition voltage can also depend on the amount of time the device has been turned off between operations, decreasing with smaller breaks in operation. Using an arbitrary qualitative scale, the value of this parameter decreases from left to right in the table, every other column. In other words, the ignition voltage decreases when the thickness of the dielectric layer is increased.

Row 15 is "Burning Voltage", which is the voltage between the electrodes that initiates sustained micro discharges after many AC cycles. This voltage is an asymptotic property, meaning the voltage that initiates micro discharges will lower from the ignition voltage and approach the burning voltage over many AC cycles. Using an arbitrary qualitative scale and comparing it to the "Ignition Voltage" row, the value of this parameter is always lower than that of the ignition voltage and decreases from left to right in the table, every other column. In other words, the burning voltage also decreases when the thickness of the dielectric layer is increased.

Row 16 is "Micro Discharge Number", which is the number of micro discharges present in the plasma gap region at any one time. Because micro discharges have a filamentary volumetric shape and all are the same size, the number of micro discharges is nearly synonymous with the momentary volume of plasma present in the plasma gap region. Using an arbitrary qualitative scale, the value of this parameter increases when traveling from left to right in the table, but at separate scales for small electrodes and large electrodes. When changing from a small electrode to a large electrode while keeping the independent variable of dielectric layer thickness constant, the value of this parameter also increases. In other words, the momentary plasma volume increases when the thickness of the dielectric layer is increased or when the surface area of the electrodes is increased.

The reason for this might be related to the decrease in burning voltage; if the applied voltage remains constant, the burning voltage threshold occurs earlier in the AC cycle where the slope of the plasma gap voltage is greater. This will cause the number of micro discharges to increase in order to cancel the rising plasma gap voltage and keep it at the value of the burning voltage more quickly. However, in some configurations, the decrease in plasma gap distance will decrease the length of each micro discharge, which might also decrease the volume of the micro discharges to a small degree. This might lead to either a smaller increase in the micro-discharge number or a decrease in micro-discharge number when increasing the thickness of the dielectric layer.

In some embodiments, there can be one or two dielectric layers between each pair of electrodes, yielding good results when there are two dielectric layers between each pair of electrodes. The number of electrodes can also vary, wherein the horizontally aligned electrodes are stacked vertically with dielectric layers and fluid gaps between every stacked electrode such that first and second electrodes serve as top and bottom electrodes to adjoin one plasma gap in a stack of electrodes and dielectric layers to create multiple plasma gaps. The number of electrodes can be configured to be between two and fifty-one, where the number of gaps between electrodes can be between one and fifty, yielding good results with the number of fluid gaps between five and twenty, and still further at ten.

The stacking process described above changes some of the parameters in the tables. The capacitance scales linearly with the number of plasma gaps, so for an arrangement of five plasma gaps, the capacitance is equal to that of a single plasma gap multiplied by five. This increase in capacitance would clearly decrease the impedance, using the formula given in the embodiments above. This would also decrease the speed of charge buildup on the electrode plate surfaces, and thus lower the plasma gap voltage between the plates. The lower plasma gap voltage would then decrease the amount of time that the plasma can be held at the burning voltage, decreasing the streamer discharge.

As indicated above, the parameters provided in the tables of FIGS. 8 and 9 are provided for exemplary purposes, and it is intended that other embodiments include other parameters.

E. Decreased Ozone Production

The chemical products of the plasma, including the relative productions of ozone versus other reactive oxygen species or free radicals, are determined at least in part by the properties of the individual micro discharges. Thus, each individual micro discharge can be regarded as a miniature non-equilibrium plasma chemical reactor. The micro discharge characteristics can be tailored for a given application, such as decreasing the relative production of ozone compared to hydroxyl radicals, by making use of the fluid properties, adjusting the electrode design, or changing the dielectric material thereby changing the properties of the dielectric layer. The properties of each micro discharge are notably independent of the electrode area or the applied voltage, which only serve to change the number of micro discharges present in the fluid gap. Thus, individual micro discharge properties are not altered during up-scaling.

From the plasma chemistry perspective, a significant or dominant characteristic of DBD is the dynamics of the electron energy distribution function (EEDF) in the micro discharge. The EEDF changes based on properties such as the value of the relative permittivity of the dielectric layer, the thickness of the dielectric layer, the electron work function of the dielectric surface, the roughness and porousness of the dielectric surface, the thickness of the fluid gap, the molecular composition of the fluid in the fluid gap, the pressure and temperature of the fluid in the fluid gap, and more. The exact proportionalities depend on the design and arrangement of the DBD.

In order to decrease the relative production of ozone compared to hydroxyl radicals, the above properties can be manipulated to increase the tail end of the EEDF (the higher energy end) above the ionization energy of fluid, including water, which leads to production of hydroxyls, but below the ionization energy of oxygen gas, which leads to ozone production. Thus, the choice of dielectric material properties, and the thickness of the dielectric layer combined with the properties of the ambient air, including water, to decrease ozone production while still producing hydroxyls for sterilization. Because ambient air conditions are held constant through all configurations of the plasma generator (for the embodiments that use ambient air as the fluid), the choice of dielectric properties can thus be selected for the ambient air conditions to achieve an optimum or enhanced EEDF.

In some embodiments, the EEDF is tailored to produce less ozone by configuring the dielectric layer with a dielectric material that has an average surface roughness between 0 nm and 800 nm. Depending on the other stated properties that affect the EEDF, good results may be yielded when a low surface roughness is desirable, between 0 and 100 nm. Good results may also be yielded when a high surface roughness is desirable, between 100 and 800 nm. Low surface roughness can be used to increase the tail end of the EEDF, and high surface roughness can accomplish the opposite. This is achieved because higher surface roughness can make the electric field near the dielectric surface very nonuniform, decreasing the burning voltage, and lowering the total electric field energy transferred to each micro discharge.

In some embodiments, the EEDF is tailored to produce less ozone by configuring the dielectric layer with a dielectric material that has a relative permittivity between 2 and 500, and a dielectric layer thickness between 0 mm and 3 mm. When the relative permittivity is on the lower end, between 2 and 15, good results for the dielectric thickness are yielded between 1 mm and 3 mm, with even better results at 2 mm. When the relative permittivity is in the middle of each end, between 15 and 100, good results for the dielectric thickness are yielded between 0 mm and 2 mm, with even better results at 1 mm. When the relative permittivity is on the higher end, between 100 and 500, good results for the dielectric thickness are yielded between 0 mm and 5 mm, with even better results at 2 mm. These combinations of relative permittivity and dielectric layer thickness affect the specific capacitance of the barrier $C_d/A$, which determines the amount of charge transferred in each micro discharge and, furthermore, the energy dissipated to the electrons in each micro discharge. These properties allow the tail end of the EEDF to be between that of the ionization energies of water and diatomic oxygen gas.

III. Sterilization System

Figure 6:
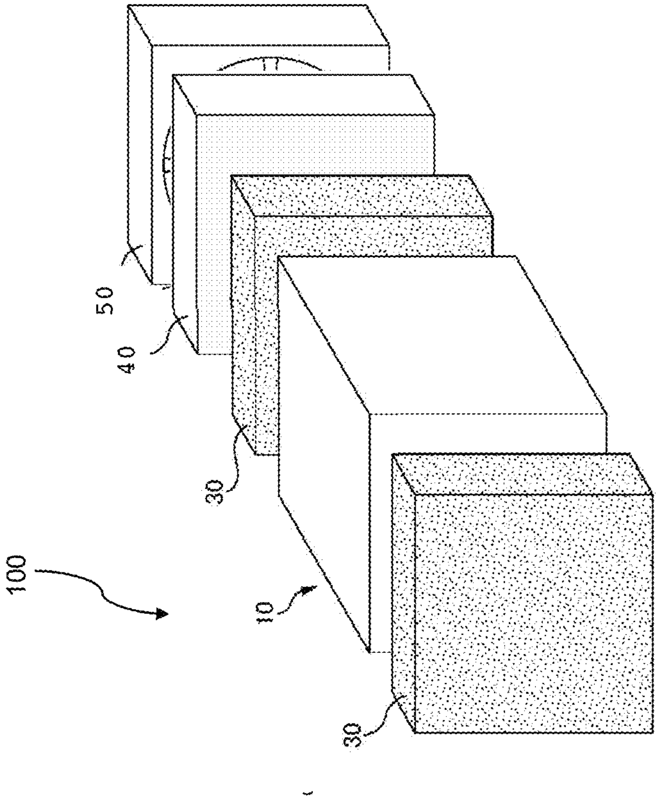
FIG. 6 is perspective view of a sterilization system 100 incorporating the plasma generator of FIG. 2.

FIG. 6 is perspective view of a sterilization system 100 incorporating the plasma generator of FIG. 2. In this sterilization system 100, the plasma generator 10 discussed above is used with other equipment to sterilize air. The plasma generator 10 used in this sterilization system 100 can be the same or similar to the embodiments discussed above, or alternatively can have differences that are incorporated to enhance performance in this application.

The sterilization system 100 includes a first ozone decomposition filter 30 at an upstream end, which filters the air prior to the air entering the plasma generator 10. Air exiting the plasma generator 10 enters a second ozone decomposition filter 30. Air exiting the second ozone decomposition filter 30 then contacts an ozone sensor 40, which is powered by a DC power supply and detects presence of ozone. A dynamic fan 50 is provided at a downstream end of the sterilization system 100 and sucks the air therethrough.

The fan 50 is a blower unit that functions as an exhaust fan of the sterilization system 100. By operating the electric fan 50 in the exhaust direction, the air inside the sterilization system 100 is introduced and passes through the plasma generator 10.

The sterilization system 100 shown in FIG. 6 arranges the various components in a linear formation, however embodiments are intended to cover other component configurations, such as the components being arranged in a circular configuration and housed within a circular-cylindrical housing.

Many reactive species are formed by the plasma generated by the plasma generator 10, including small amounts of Ozone (O3), which is potentially harmful to humans (having a unique odor) and could exit in either an upstream direction of a downstream direction absent mitigation efforts.

Thus, the ozone decomposing filters 30 are provided at the upstream and downstream sides of the plasma generator 10. The ozone decomposing filters 30 reduce, minimize, or prevent the ozone from exiting back through the upstream side or through the downstream side of the sterilization system 100. However, in some embodiments where there is no issue with ozone flowing back through the upstream flow path, the ozone decomposing filter 30 at the upstream side can be eliminated.

Embodiments are intended to include any related art, known, or later developed ozone-degrading filters for this purpose. The shape and dimensions of the ozone decomposing filters 30 depend on the specifications of the sterilization system 100 in which they are incorporated.

An ozone sensor 40 is provided downstream of the plasma generator 10 and the second ozone decomposition filter 30 adjacent the fan 50 to confirm proper operation of the ozone decomposition filters 30, and thus compliance with safety standards. For example, regulations provide that the permissible concentration in a work environment is approximately 0.1 ppm or less, as per Japanese, US, European, or other standards.

The ozone sensor 40 measures the ozone concentration contained in the exhaust gas on the downstream side of plasma generator 10. Embodiments are intended to include any related art, known, or later developed ozone sensor 40, such as a semiconductor type gas sensor with a high sensitivity. By monitoring the force, the ozone sensor 40 can be configured to control the operation of the plasma generator 10 such as to cease operations of the plasma generator 10 should it detect improper amounts of ozone. However, some embodiments do not include an ozone sensor 40, such as those that integrate an AQRSS, as referred to above.

Figure 7:
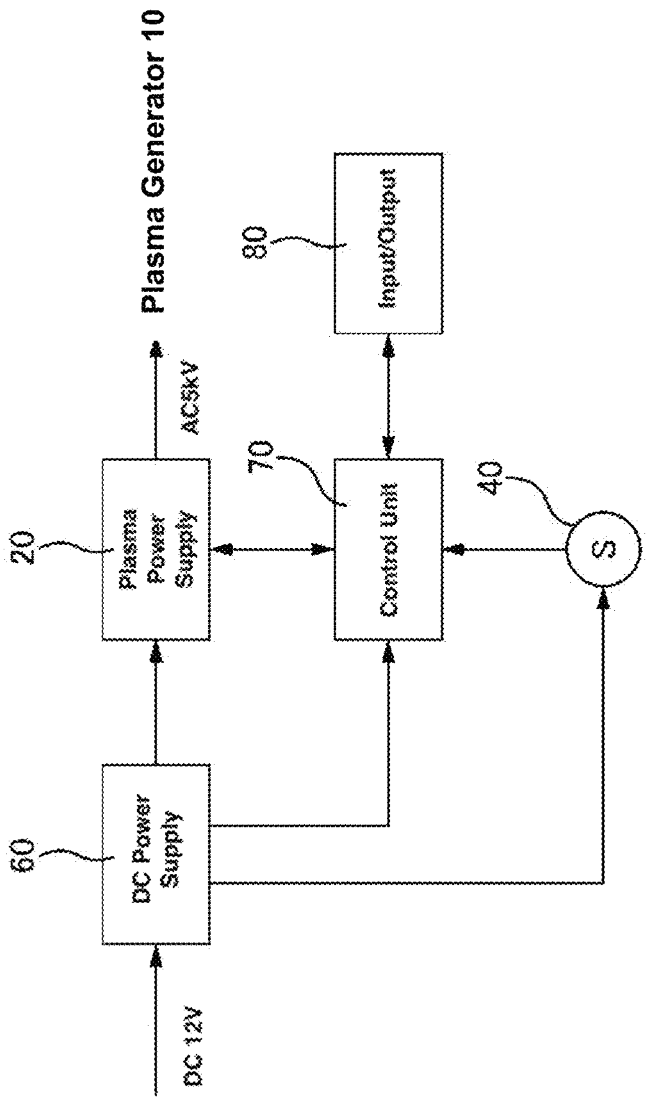
FIG. 7 is a schematic of an exemplary control circuit for the sterilization system 100 of FIG. 6.

FIG. 7 is a schematic of an exemplary control circuit for the sterilization system 100 of FIG. 6. As shown in FIG. 7, 12V DC is supplied to the DC power supply 60, which then supplies DC voltage to the control unit 70 as well as to the plasma power supply 20. The control unit 70 is also directly connected to the plasma power supply 20.

The DC power supply 60 is configured to supply a variety of DC voltages to the plasma power supply 20 and to the control unit 70. For example, the DC power supply 60 can supply DC 24V and DC 5V to power the control unit 70 and can supply DC 12V to the plasma power supply 20. The plasma power supply 20 converts the received DC 12V to AC, such as 5 kV AC, which it supplies to the plasma generator 10. The control unit 70 is also configured to communicate with the Input/output 80.

What is claimed is:

1. A plasma generator for generating atmospheric pressure, low temperature plasma, comprising:

a first electrode that defines a planar bottom surface, the first electrode having a width and length that are each greater than a height extending in a height direction that is perpendicular to the planar bottom surface;

a second electrode that defines a planar top surface, the second electrode having a width and length that are each greater than a height extending in the height direction that is perpendicular to the planar top surface, the second electrode opposing the first electrode such that the bottom surface of the first electrode faces the top surface of the second electrode;

a first dielectric layer that is disposed on at least a part of the bottom surface of the first electrode, the first dielectric layer having a relative permittivity between 2 and 15, and a thickness between 1 mm and 3 mm, the first dielectric layer having a first peripheral region;

a second dielectric layer that is disposed on at least a part of the top surface of the second electrode, the second dielectric layer having a relative permittivity between 2 and 15, and a thickness between 1 mm and 3 mm, the second dielectric layer having a second peripheral region;

a spacer disposed between the first and second peripheral regions of the first dielectric layer and the second dielectric layer and configured to support the first and second electrodes so as to define a predetermined gap between the first and second dielectric layers, wherein the spacer is configured such that the generated plasma extends across a central region between the first and second dielectric layers that is free of spacer material and the spacer is disposed outside the central region, and the predetermined gap is between about 1.5 mm and 3.0 mm; and a power supply configured to supply electrical power to the first and second electrodes at a predetermined voltage and frequency, such that, based on the predetermined gap between the first and second dielectric layers, low temperature plasma is stably generated at atmospheric pressure without arc discharge, wherein the dielectric layers are configured to inhibit arc discharge while maintaining the low-temperature plasma generation.

2. The plasma generator of claim 1, wherein the power supply is configured to supply AC electrical power, and to be adjustable to provide desired AC voltages to generate stable atmospheric pressure, low temperature plasma.

3. The plasma generator of claim 1, wherein the power supply includes an inverter that is configured to converts DC voltage to AC voltage and is configured to output AC20V-AC100V.

4. The plasma generator of claim 3, wherein the inverter is configured to output AC25V-AC45V.

5. The plasma generator of claim 4, wherein the inverter is configured to output AC30V-AC35V.

6. The plasma generator of claim 5, wherein the inverter is configured to output AC33.3V.

7. The plasma generator of claim 3, wherein the inverter is configured to output an applied voltage with a frequency ranging from 30 Hz-90 Hz.

8. The plasma generator of claim 7, wherein the inverter is configured to output an applied voltage with a frequency ranging from 50 Hz-70 Hz.

9. The plasma generator of claim 8, wherein the inverter is configured to output an applied voltage with a frequency that is 60 Hz.

10. The plasma generator of claim 3, wherein the power supply includes a booster that receives the output of the inverter and boosts the received voltage at a rate of 150× at 2× intervals, ranging from 3 kV-15 kV.

11. The plasma generator of claim 10, wherein the booster boosts the applied voltage at a rate of 150× at 2× intervals, ranging from 4 kV-7.5 kV.

12. The plasma generator of claim 11, wherein the booster boosts the applied voltage at a rate of 150× at 2× intervals that is 5 kV.

13. The plasma generator of claim 1, further comprising a fan configured to move gas to contact the generated plasma, and an ozone decomposition filter to separate ozone from the gas that has contacted the generated plasma.

14. The plasma generator of claim 1, wherein, for each of the first and second dielectric layers, the thickness is between 1 mm and 2 mm.

15. The plasma generator of claim 1, wherein the first electrode defines a top surface that is parallel to the bottom surface of the first electrode, the plasma generator further comprising:

a supplemental first dielectric layer that is disposed on at least a part of the top surface of the first electrode, the supplemental first dielectric layer having a relative permittivity between 2 and 500, and a thickness of 3 mm or less;

a third electrode that defines a planar bottom surface, the third electrode having a width and length that are each greater than a height extending in the height direction that is perpendicular to the planar bottom surface; and a third dielectric layer that is disposed on at least a part of the bottom surface of the third electrode, the third dielectric layer having a relative permittivity between 2 and 500, and a thickness of 3 mm or less, wherein the spacer is configured to support the third electrode so as to define a second predetermined gap between the supplemental first dielectric layer and the third dielectric layer, and is disposed between peripheral regions of the dielectric layers, the power supply is configured to supply electrical power to all electrodes, including the third electrode, at the predetermined voltage and frequency, such that, based on the second predetermined gap between the supplemental first dielectric layer and the third dielectric layer, atmospheric pressure, low temperature plasma is; and wherein the first, second, and third electrodes define multiple parallel atmospheric pressure plasma generation regions.

16. The plasma generator of claim 1, wherein the power supply is configured to apply an alternating voltage of 3 to 10 kV at a frequency between 10 kHz and 100 kHz.

17. The plasma generator of claim 1, wherein the spacer comprises a dielectric material having a relative permittivity between 3 and 10.

18. The plasma generator of claim 1, wherein the predetermined gap is less than or equal to the thickness of each of the first and second dielectric layers.

19. The plasma generator of claim 18, wherein the predetermined gap and the thicknesses of the dielectric layers are selected to maintain dielectric barrier discharge operation at atmospheric pressure without transition to arc discharge.

20. The plasma generator of claim 19, wherein the first and second dielectric layers define opposing planar plasma generation surfaces extending continuously across a plasma generation area.

21. The plasma generator of claim 20, wherein the plasma generator operates at less than 60 watts.

* * * * *